US010770176B2

United States Patent
Simon et al.

(10) Patent No.: US 10,770,176 B2
(45) Date of Patent: Sep. 8, 2020

(54) SYSTEM AND METHOD FOR IDENTIFYING RELATIONSHIPS IN COMMUNITY HEALTHCARE MEASURES

(71) Applicant: Optum, Inc., Minnetonka, MN (US)

(72) Inventors: Carol Jean Simon, Edina, MN (US); Paul A. Bleicher, Newton, MA (US); John Edward Hargraves, Washington, DC (US); Paul John Wallace, Piedmont, CA (US)

(73) Assignee: Optum, Inc., Minnetonka, MN (US)

( * ) Notice: Subject to any disclaimer, the term of this patent is extended or adjusted under 35 U.S.C. 154(b) by 896 days.

(21) Appl. No.: 14/661,775

(22) Filed: Mar. 18, 2015

(65) Prior Publication Data

US 2016/0026942 A1    Jan. 28, 2016

Related U.S. Application Data

(63) Continuation-in-part of application No. 14/565,808, filed on Dec. 10, 2014, now Pat. No. 10,438,701.
(Continued)

(51) Int. Cl.
*G16H 40/20* (2018.01)
*G16H 15/00* (2018.01)
(Continued)

(52) U.S. Cl.
CPC .......... *G16H 40/20* (2018.01); *G06F 19/328* (2013.01); *G06Q 10/0631* (2013.01);
(Continued)

(58) Field of Classification Search
CPC .. G06F 19/328; G06Q 50/22; G06Q 10/0631; G16H 40/20; G16H 50/80; G16H 15/00
See application file for complete search history.

(56) References Cited

U.S. PATENT DOCUMENTS

2002/0123909 A1    9/2002  Salisbury
2004/0225200 A1    11/2004 Edmunson et al.
(Continued)

OTHER PUBLICATIONS

Sopan et al., Community Health Map: A geospatial and multivariate data visualization tool for public health datasets, 2012, Government Information Quarterly, pp. 1-12. (Year: 2012).*

*Primary Examiner* — Christopher L Gilligan
(74) *Attorney, Agent, or Firm* — Seyfarth Shaw LLP; Brian Michaelis

(57) ABSTRACT

A system and method for identifying relationships and correlations between community healthcare attributes includes automatically displays relationships between selected community health measures. A correlation tool automatically computes correlations between a selected main measure and each other measures in a set of community health measures for selected communities. The correlation tool automatically displays a ranked list of the other community health measures based on their correlation to the selected main measure. A relationship tool automatically computes correlations between selected measures in the set of community health measures for selected communities. The relationship tool displays a correlation graph indicating values of the selected measures for each of a selected set of communities. An adjusted correlation graph is automatically displayed to indicate adjusted values of the selected measures to accommodate a selected third measure as a control variable.

18 Claims, 14 Drawing Sheets

Related U.S. Application Data

(60) Provisional application No. 62/048,082, filed on Sep. 9, 2014, provisional application No. 62/028,627, filed on Jul. 24, 2014.

(51) Int. Cl.
    *G16H 50/80*     (2018.01)
    *G06Q 50/22*     (2018.01)
    *G06F 19/00*     (2018.01)
    *G06Q 10/06*     (2012.01)

(52) U.S. Cl.
    CPC ............ *G16H 15/00* (2018.01); *G16H 50/80* (2018.01); *G06Q 50/22* (2013.01)

(56) References Cited

U.S. PATENT DOCUMENTS

| | | |
|---|---|---|
| 2005/0234742 A1 | 10/2005 | Hodgdon |
| 2008/0184097 A1 | 7/2008 | Tarkka et al. |
| 2010/0082362 A1* | 4/2010 | Salsbury ............ G06F 19/3431 705/1.1 |
| 2011/0161857 A1* | 6/2011 | Kramer ................ G06T 11/206 715/772 |
| 2012/0303381 A1 | 11/2012 | Bessette |
| 2013/0158968 A1 | 6/2013 | Ash et al. |
| 2014/0100880 A1* | 4/2014 | Patterson ............ G06F 19/327 705/3 |
| 2014/0379520 A1* | 12/2014 | Nemery ............ G06Q 30/0631 705/26.7 |
| 2015/0105647 A1* | 4/2015 | Katra .................. A61B 5/0537 600/391 |

\* cited by examiner

US Community Health Viewer

© 2014 Optum Labs. All rights reserved.

Choose HRRs to view:
All
Load HRRs    Clear HRRs

Choose aggregate measure:
Economic Performance

Choose individual measure:
% in Poverty

Choose:
● Inputs
○ Outcomes
○ Other Demographics

Number of communities to view:
306

Order:
● Favorable
○ Unfavorable

Choose region to view:
National

Choose type of selection:
● Region
○ State

Map | Data Table | Heat Map | Correlations | Relationship

Find Correlations to the Main Variable 838

Choose positive or negative slope of relationship:
● Positive ○ Negative

IMPORTANT: All non-demographic variables are arranged so that higher values are more favorable. In many cases, the axis may be "reversed" from what might be expected. Example: For "% in Poverty," 100% would be at the origin, and 0% would be at the extreme of the x-or y-axis.

10 ▼ records per page            Search: [        ]
    836                                        832           834

| Rank | ♦ Measure | ♦ R2 |
|---|---|---|
| 1 | % of Children in Poverty | 0.909 |
| 2 | Economic Performance (Aggregate) | 0.773 |
| 3 | % Receiving SNAP | 0.682 |
| 4 | Median Household Income | 0.603 |
| 5 | % Reporting Poor or Fair Health | 0.568 |
| 6 | % High School Graduates | 0.522 |
| 7 | Social Capital (Aggregate) | 0.500 |
| 8 | Population Health (Aggregate) | 0.476 |
| 9 | Years of Productive Life Lost | 0.431 |
| 10 | Hypertension Medication Adherence | 0.393 |

| Rank | Measure | R2 |

Showing 1 to 10 of 94 entries          ← Previous  1  2  3  4  5  Next →

FIG. 8

SYSTEM AND METHOD FOR IDENTIFYING RELATIONSHIPS IN COMMUNITY HEALTHCARE MEASURES

CROSS REFERENCE TO RELATED APPLICATIONS

The present application is a Continuation-in-Part of U.S. patent application Ser. No. 14/565,808 entitled COMMUNITY HEALTH SCORING TOOL which was filed on Dec. 10, 2014, which claims the priority of U.S. Provisional Patent Application No. 62/028,627 entitled COMMUNITY HEALTH SCORING TOOL which was filed on Jul. 24, 2014 both of which are incorporated herein by reference in their entirety. The present application also claims the priority of U.S. Provisional Patent Application No. 62/048,082 entitled COMMUNITY HEALTH SCORING TOOL which was filed on Sep. 9, 2014 and which is incorporated herein by reference in its entirety.

FIELD OF TECHNOLOGY

The present disclosure relates generally to healthcare information processing and particularly to systems and frameworks for measuring healthcare resource distribution.

BACKGROUND

A large amount of consumer healthcare information is routinely collected by healthcare providers, insurance providers, government agencies, researchers and other institutions. Even though much of the information is stored electronically, analyzing the information to improve healthcare delivery generally involves extensive efforts to identify appropriate data sources and to secure access to the data sources. Useful healthcare information may be stored on diverse computer networks and data storage systems, which may often be difficult or impossible to access for research purposes. Refining or expanding research efforts to analyze different parameters may often involve repeated efforts to access different data sources. Due to these and other difficulties, useful data representations that are suitable to support decisions for healthcare resource allocation in various communities have heretofore been scarce.

SUMMARY

A method for measuring community healthcare attributes according to an aspect of the present disclosure includes storing a first collection of healthcare data in one or more electronic storage systems. The first collection includes a number of health outcomes for healthcare consumers in a number of communities. The healthcare outcomes may include measures of healthcare cost, healthcare quality, and population health, for example.

A system for measuring healthcare related characteristics of a population segment according to another aspect of the present disclosure includes one or more electronic data storage systems coupled in electronic communication with one or more healthcare data sources. The system also includes a community healthcare database stored in one or more of the electronic data storage system(s) and one or more processors coupled in electronic communication with the electronic data storage systems. The community healthcare database includes a first collection of healthcare data. The first collection includes health outcomes for healthcare consumers in a number of communities, in which the healthcare outcomes for each consumer are associated with one or more of the communities. A second collection of community data is also stored in the electronic data storage system(s). The second collection includes population attributes that characterize the populations of healthcare consumers, resources, infrastructure and/or environment in each of the communities. The processor(s) are configured for receiving a first interactive input that selects one or more of the healthcare outcomes and/or one or more of the population attributes, identifying a correlation between the selected healthcare outcomes and one or more of the population attributes by accessing the first collection of healthcare data and the second collection of community data in response to receiving the interactive inputs, and representing the correlation to a user.

A method of measuring community healthcare characteristics according to another aspect of the present disclosure includes receiving one or more healthcare outcomes for each of a number of communities, automatically scoring each of the communities based on the corresponding healthcare outcomes and displaying a representation of the communities arranged based on their score.

A method for measuring community healthcare attributes, according to another aspect of the present disclosure includes storing a collection of healthcare data in one or more electronic storage systems. The collection of healthcare data includes a health outcomes for healthcare consumers in a number of communities and/or population attributes of the communities. The method includes associating the healthcare outcomes and/or population attributes for each consumer with one or more of the communities to generate a community healthcare database.

Additional features and advantages of the present disclosure are described below. It should be appreciated by those skilled in the art that this disclosure may be readily utilized as a basis for modifying or designing other structures, systems and processes for carrying out the same purposes of the present disclosure. It should also be realized by those skilled in the art that such equivalent implementations do not depart from the teachings of the disclosure as set forth in the appended claims. The novel features, which are believed to be characteristic of the disclosure, both as to its organization and method of operation, together with further objects and advantages, will be better understood from the following description when considered in connection with the accompanying figures. It is to be expressly understood, however, that each of the figures is provided for the purpose of illustration and description only and is not intended as a definition of the limits of the present disclosure.

BRIEF DESCRIPTION OF THE DRAWINGS

The particular features and advantages of the present disclosure will be apparent from the detailed description set forth below in conjunction with the drawings in which like reference characters identify corresponding aspects throughout.

FIG. 8 is an illustration of a correlation tool user interface according to aspects of the present disclosure.

DETAILED DESCRIPTION

The features and advantages of the present disclosure will become apparent from the following detailed description of illustrative embodiments thereof, which is to be read in connection with the accompanying drawings.

Computer systems may be coupled together in various ways to enable communications between them, including being coupled together in networks such as local area networks (LANs), wide area networks (WANs), or combinations of networks, such as the Internet and world wide web. Data may be transferred (e.g., copied or moved) between computer systems in various ways. For instance, an application executing at a first computer system may generate a query, which is a request for particular data. The query may be transmitted to a second computer system, which contains or has access to a data source containing the desired data. The second computer system responds to the query by transmitting the requested data to the first computer system.

The present specification discloses one or more embodiments that incorporate the features of the invention. The disclosed embodiment(s) merely exemplify the invention. The scope of the invention is not limited to the disclosed embodiment(s). The invention is defined by the claims appended hereto.

References in the specification to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described.

Figure 1:
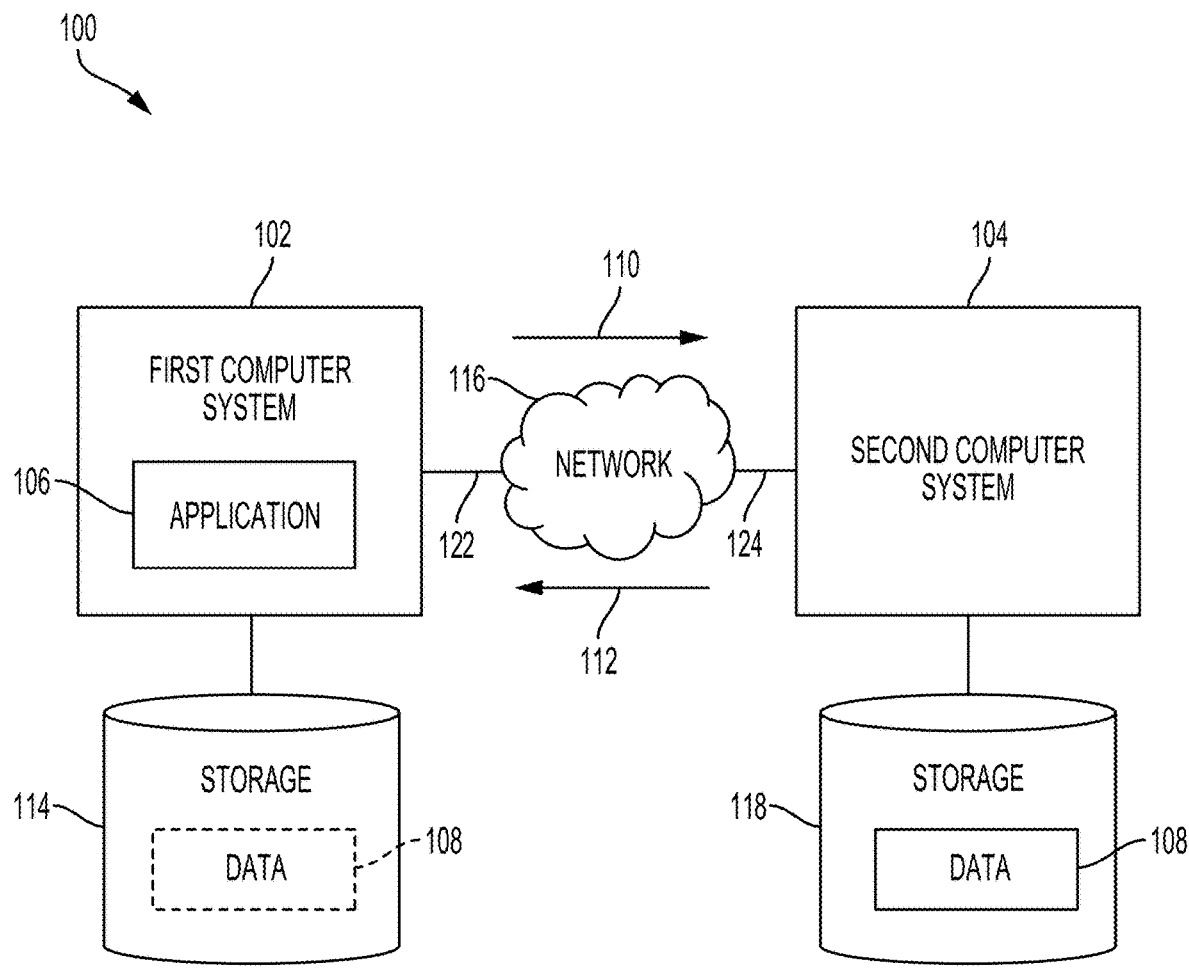
FIG. 1 shows a block diagram of a data communication system according to aspects of the present disclosure.

Aspects of the present disclosure relate to data communications in distributed systems. For example, FIG. 1 shows a block diagram of a data communication system 100, according to an example embodiment. As shown in FIG. 1, system 100 includes a first computer system 102, a second computer system 104, a first storage 114, a network 116, and a second storage 118. An application 106 executes in first computer system 102. Storage 114 is coupled to first computer system 102. Storage 118 is coupled to second computer system 104. First and second computer systems 102 and 104 are communicatively coupled by network 116. System 100 is configured to enable resources to be transferred between first and second computer systems 102 and 104.

First and second computer systems 102 and 104 may each be any type of computing device, including a desktop computer (e.g., a personal computer), a server, a mobile computer or computing device such as a smart phone or tablet computer device, a personal digital assistant (PDA), a laptop computer, a notebook computer, etc., or other type of computer system. Storage 114 and storage 118 may each include one or more of any type of storage mechanism to store content (e.g., objects), including a hard disk drive, an optical disc drive, a memory device such as a RAM device, a ROM device, etc., and/or any other suitable type of storage medium.

Network 116 may include one or more communication links and/or communication networks, such as a LAN (local area network), a WAN (wide area network), or a combination of networks, such as the Internet. First and second communication links 122 and 124, which respectively couple first and second computer systems 102 and 104 to network 116, may include any number of communication links, including wired and/or wireless links, such as IEEE 802.11 wireless LAN (WLAN) wireless links, Worldwide Interoperability for Microwave Access (Wi-MAX) links, cellular network links, wireless personal area network (PAN) links (e.g., Bluetooth™ links), Ethernet links, USB links, etc.

Application 106 may issue a query for a resource (e.g., data). The resource may be accessible as data 108 contained in storage 118 at second computer system 104. To obtain the resource, first computer system 102 may transmit the query from first computer system 102 in a first communication signal 110. For example, first computer system 102 may contain an agent (e.g., a "client" agent) configured to handle transmission of queries. First communication signal 110 is transmitted through a first communication link 122, network 116, and a second communication link 124, and is received by second computer system 104. First communication signal 110 may be transmitted in any form, including in the form of a stream of packets (e.g., IP packets).

Second computer system 104 processes the request received in first communication signal 110. For example, second computer system 104 may include an agent (e.g., a "server" agent) configured to process received queries. Second computer system 104 retrieves data 108 from storage 118, which may contain a database or other data source. Second computer system 104 generates a second communication signal 112, which is a response signal that includes data 108. Second communication signal 112 is transmitted through second communication link 124, network 116, and first communication link 122, and is received by first computer system 102. Application 106 receives data 108 included in second communication signal 112, which may be stored in storage 114 (as indicated by dotted lines in FIG. 1). Second communication signal 112 may be transmitted in any form, including in the form of a stream of packets (e.g., IP packets).

Currently, applications and services are being developed that include the use of REST (representational state transfer) interfaces for accessing resources and a URI (Uniform Resource Identifier) namespace that identifies the resources.

These applications and services enable web-based data sources to be accessed in a more efficient manner. For example, second computer system 104 in FIG. 1 may be configured to have a REST interface to enable data 108 to be accessed according a URI.

Figure 2:
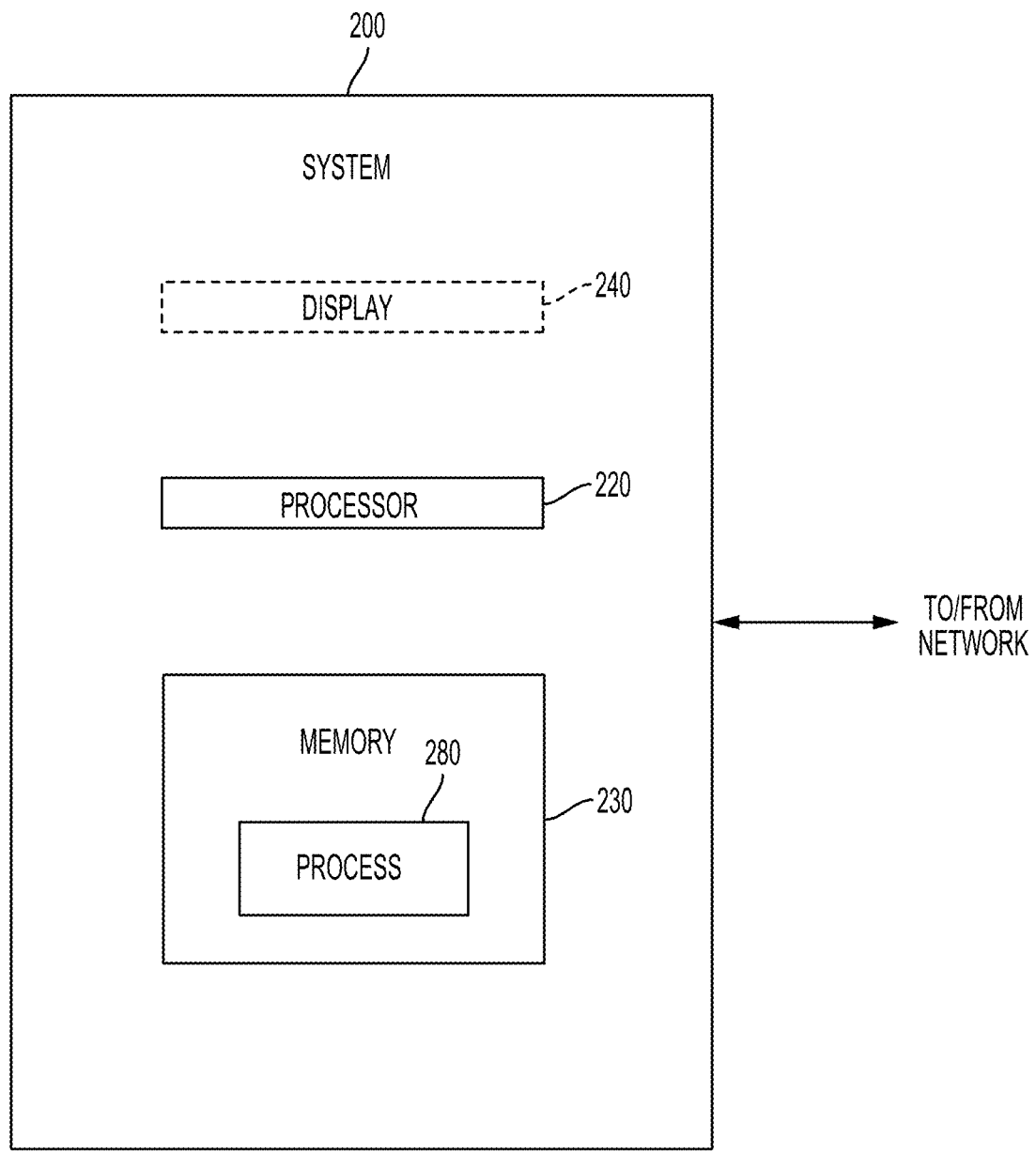
FIG. 2 is a block diagram of a system that can implement part or all of one or more aspects or processes of systems to implement a community health measures tool according to embodiments of the present disclosure.

FIG. 2 is a block diagram of a system 200 that can implement part or all of one or more aspects or processes of systems within which a web-native bridge according to embodiments of the present disclosure can operate or within which methods according to embodiments of the present disclosure can be carried out. As shown in FIG. 2, memory 230 configures the processor 220 to implement one or more aspects of the methods, steps, and functions disclosed herein (collectively, shown as process 280 in FIG. 2). Different method steps can be performed by different processors. The memory 230 could be distributed or local and the processor 220 could be distributed or singular. The memory 230 could be implemented as an electrical, magnetic or optical memory, or any combination of these or other types of storage devices. It should be noted that if distributed processors are employed, each distributed processor that makes up processor 220 generally contains its own addressable memory space. It should also be noted that some or all of computer system 200 can be incorporated into an application-specific or general-use integrated circuit. For example, one or more method steps could be implemented in hardware in an ASIC rather than using firmware. Display 240 is representative of a variety of possible input/output devices (e.g., displays, touchscreens, mice, keyboards, and so on).

A system for measuring health care related characteristics of a population segment according to an aspect of the present disclosure includes one or more electronic data storage systems coupled in electronic communication to one or more health care data sources. The electronic data storage systems may be coupled to the health care data sources directly or indirectly by one or more different means for communication such as direct wiring, wireless communication, fiber optics, and may involve communication via one or more intermediate communication network such as the Internet, for example. The health care data sources may include various entities, groups or networks that are involved with the healthcare industry and which generate, receive and/or collect healthcare related information. Healthcare data sources may include healthcare providers, healthcare payers, researchers and/or government agencies, for example.

Because a large amount of healthcare data may at times be subject various strict privacy policies, regulations or statutes governing the storage and communication private healthcare information, aspects of the present disclosure include systems that may not be configured in a standard technical environment using only standard communication techniques, conventional general purpose computer networks and communication equipment, for example. Rather, aspects of the present disclosure may provide substantial improvements to the conventional technical environments for accessing, storing and/or communicating healthcare information include special purpose computer hardware, software, algorithms and/or communication techniques to de-identify data and/or to ensure that healthcare data is accessed, communicated and stored in a manner that private healthcare data may include private health information. For example, the system may include special purpose computer hardware, software, algorithms and/or communication techniques or portions thereof that may be implemented by only a small number of healthcare industry stakeholders such as healthcare payer and provider networks to ensure data privacy.

According to aspects of the present disclosure, the system includes a community health care database stored in one or more of the electronic data storage system(s) and one or more processors coupled in electronic communication with the electronic data storage systems. In this implementation, the community health care database includes a first collection of health care data. The first collection includes health outcomes for health care consumers in a number of communities, in which the health care outcomes for each consumer are associated with one or more of the communities. A second collection of community data is also stored in the electronic data storage system(s). The second collection includes population attributes that characterize the populations of healthcare consumers, resources, infrastructure and/or environment in each of the communities. The processor(s) are configured for receiving a first interactive input that selects one or more of the health care outcomes and/or one or more of the population attributes, identifying a correlation between the selected health care outcomes and one or more of the population attributes by accessing the first collection of health care data and the second collection of community data in response to receiving the interactive inputs, and representing the correlation to a user.

According to an aspect of the present disclosure a database of previously unavailable community healthcare measures is generated by accessing sources of electronic healthcare data via communication links to one or more healthcare networks, for example, processing a wide variety of the healthcare data to compute population health outcomes for numerous communities and combing the population health outcomes with community data from numerous data sources.

The community data describes a large number of communities in terms of various population attributes. The population attributes include demographic population characteristics of each community as well as healthcare delivery system attributes for each community. The healthcare delivery system attributes may characterize system of health care, healthcare infrastructure and environment, for example. Examples of various population attributes that may be used to generate the disclosed healthcare measures database according to aspects of the present disclosure are listed in Table 1.

TABLE 1

| Population characteristics | Delivery System Attributes |
| --- | --- |
| Social Capital | Capacity |
| Predicted mean health literacy | Primary care providers/100,000 |
| % with basic health literacy or above | Specialist MDs/100,000 |
| % high school graduates | Hospital beds/1,000 |
| Petris social capital | Ambulatory centers/100,000 |
| Per capita 501c3 revenues - regional non-profit activity | Nurses/1000 |
| | PAs/1000 |
| Aggregate social capital - emotional support | Incentives |

TABLE 1-continued

| Population characteristics | Delivery System Attributes |
|---|---|
| % college graduates | % hospitals with salaried physician arrangements |
| Economics | % hospital revenues from capitations |
| Median household income Change in income 2000 to 2009 Unemployment rate | Managed care penetration |
| Employers and employment | % hospital revenues at risk |
| Demographics | Integration and Alignment |
| Race and ethnicity (1% distribution) % population living in rural area | % hospitals with CPHO physician arrangements |
| | % hospitals with OPHO physician arrangements |
| Health behaviors: | % physicians working in hospital owned practices |
| Smoking rate | % physicians working in health system owned practices |
| Chlamydia infections/1,000 | |
| Average life expectancy | % physicians working in large (50+) practices |
| Obesity rate | % physicians in solo practice |
| | % physicians in IPAs |
| | % hospitals with IPAs |
| | ACO & PCMH coverage |
| | HIT |
| | % hospitals with electronic health records |
| | % hospitals with health information exchanges |
| | % hospitals with EMRs achieving MU |
| | % primary care providers receiving HIT incentive$ |

Examples of various healthcare outcomes that may be used to generate the disclosed healthcare measures database according to aspects of the present disclosure are listed in Table 2.

TABLE 2

| | |
|---|---|
| Preference-Sensitive (PS) Care: "choosing wisely" | Appropriate Care |
| PS cholecystectomy procedures/1,000 | Adherence to clinical guidelines - appropriate prescribing |
| PS back surgery procedures/1,000 | Adherence to clinical guidelines - Physician follow up |
| PS hysterectomy for uterine fibroid procedures/1,000 | Adherence to clinical guidelines - pregnancy lab screening |
| PS lower extremity bypass procedures/1,000 | Adherence to clinical guidelines - testing medication complications |
| PS carotid endarterectomy procedures/1,000 | |
| PS angiography procedures/1,000 | |
| PS CABG procedures/1,000 | Adherence to clinical guidelines - screening chronic conditions |
| PS high tech diagnostic imaging/1,000 | |
| PS prostatectomy procedures/1,000 | Medication Adherence (commercial) |
| PS AAA procedures/1,000 | Asthma medication adherence |
| PS pacemaker insertion procedures/1,000 | Depression medication adherence |
| PS PCI/PTCA procedures/1,000 | CAD medication adherence |
| PS bone marrow/organ transplants/1,000 | Diabetes medication adherence |
| PS C-section rate | Hyperlipidemia medication adherence |
| PS mastectomy/1,000 | Hypertension medication adherence |
| PS total knee replacement procedures/1,000 | Costs of Care - total and by site, type |
| PS mitral-aortic valve procedures/1,000 | Commercial costs -adjusted for age, gender, and input prices |
| PS total shoulder replacement/1,000 | |
| PS total hip replacement/1,000 | Medicare costs adjusted for age, gender, and risk |
| Medicare preference sensitive knee replacements/1,000 | Prevalence of disease |
| | Prevalence depression/1,000 |
| Medicare preference sensitive hip replacements/1,000 | Prevalence of lower back problems/1,000 |
| | Prevalence of migraine |
| Medicare preference sensitive back surgery/1,000 | Prevalence of COPD/1,000 |
| Avoidable Care | Prevalence of hypertension/1,000 |
| Readmissions rate- commercial | Prevalence of diabetes/1,000 |
| Avoidable admissions/1,000, commercial | Prevalence of CHF/1,000 |
| Medicare avoidable admissions | Prevalence of ESRD/1,000 |
| Medicare readmission rate | Prevalence of CAD/1,000 |
| Avoidable ED visits/1,000 | Utilization |
| | ED visits/1,000 |
| | Office visits/1,000 |
| | Inpatient admissions |

According to aspects of the present disclosure, a community may include a geographical area, a demographic group within a population, a group of healthcare providers or other stakeholders, for example.

The community health measures include measures of health care cost, healthcare quality and community characteristics. Examples of the community characteristic that are combined with healthcare data to generate community health measures according to aspects of the present disclosure include socioeconomic status, economic activity, economic growth, social capital, structure and capacity of healthcare delivery systems, alignment of healthcare providers, incentives for healthcare stakeholders and adoption of healthcare information technology (HIT).

According to the present disclosure, the community healthcare measures are constructed based on data received from a number of public sources and proprietary sources. In one example, data received from public sources includes socioeconomic status (SES), economics, social capital information that is extracted from census and from the American Community Survey performed by the United States Census Bureau. According to aspects of the present disclosure, measures of health outcomes and healthcare costs are computed based on claims data that is electronically compiled by insurance providers such as United HealthCare of Minnetonka, Minn. Other measures of healthcare outcomes and costs may be computed based on data received from healthcare provider networks and medical associations such as the American Hospital Association, for example. Additional data for computing health outcomes and healthcare costs may be received from primary data collection performed by accountable care organizations in the community, for example. According to aspects of the present disclosure, data from any one or combination of these public and private data sources may be accessed to generate various health care measures.

The community health measures database that is generated according to aspects of the present disclosure may be used by stakeholders and policy makers in government and throughout the healthcare industry to improve healthcare delivery by increasing efficiency of healthcare networks, improving allocation of healthcare resources, and enhancing development, testing and deployment of healthcare innovations.

According to aspects of the present disclosure, the disclosed community health measures database is accessed to define and compute numerous new community health measures including: a community health measure that characterizes the structure of the delivery system; a community health measure that characterize supply of medical providers; a community health measure that characterize innovations in an organization of care; a community health measure that characterizes HIT adoption; a community health measure that characterizes health care costs; a community health measure that characterizes resource utilization; and a community health measure that characterizes appropriate care in the commercial population based on analysis of health insurance data, for example.

According to another aspect of the present disclosure, the community health measures database is incorporated in and/or accessed by a community health care measures tool. The community health measures tool leverages aspects of the community health measure database to generate previously unavailable representations of community health information. A community health measures tool according to aspects of the present disclosure may be implemented on personal computers, computer networks and/or mobile devices, for example.

One implementation of a community health measures tool according to aspects of the present disclosure includes a community measures scoring tool. The community healthcare scoring tool may be configured to score communities based on their attainment of desirable health outcomes and/or based on availability of healthcare resources that attribute to desirable health outcomes, for example. Performance scores and ranking of the communities is computed by accessing and statistically processing selected population attributes of the communities in the community health measures database.

According to an aspect of the present disclosure user-defined weights for particular population attributes and/or healthcare outcomes may be predefined or received by interactive input to customize the rankings according to user needs and criteria. In this implementation, users may define the weights to customize the computation and/or representation of community rankings. The community scores, rankings, and comparative similarity with respect to selected health outcomes and population attributes may be interactively computed to support a wide range of a number of business and clinical decisions.

A community health measures tool according to an aspect of the present disclosure includes a computer implemented application configured with a graphical user interface for receiving a selection and weighting of communities, population attributes and/or healthcare outcomes, and displaying a representation of the selected communities, population attributes and/or healthcare outcomes. The representation is computed and displayed by processing data in a healthcare measures database based on the selections and weightings of communities, population attributes and/or healthcare outcomes.

In one example, the community measures scoring tool is configured to represent community efficiency scores by receiving and/or computing composite healthcare input measures and composite health outcomes for each of a number of communities based on the population attributes and health outcomes in the community health measures database. The composite healthcare input measures and composite health outcome measures are statistically processed to generate scores that represents an efficiency measure for each respective community.

According to aspects of the present disclosure, selected community scores may be juxtaposed in a map display, represented in a table, or arranged in a heat map to identify similar communities, for example. A map display according to aspects of the present disclosure may be color coded or shaded to represent selected community scores with respect to selected health outcomes and/or community attributes. In one example, the tool may be configured to display a color of a community on a map to represent a number of standard deviations of the corresponding community's score from a mean community score in a selected health care measure. In another example, the tool may be configured to display a color of each community on a map to represent the percentile or decile of scores in all communities in which the respective communities scored with respect to a particular healthcare measure, for example. In table display according to aspect of the present disclosure may display a list of communities ranked by their score in a selected health care measure.

Alternatively the community measures scoring tool may be configured to display a heat map representation of community scores. The heat map representation displays a color coded or shaded grid in which colors and/or shading of grid elements represent relative scores attained by each of a number of selected communities in each of a number of selected health outcomes and/or population attributes. According to another aspect of the present disclosure, a clustering process may be used to cluster together certain healthcare outcomes and/or population attributes. The clustering process may be used to generate a heat map representation, which identifies factors that act similarly in a particular group of communities, and which identifies communities that are most similar to each other, for example.

Implementations of the disclosed community measures scoring tool may be used to identify communities that are similar or dissimilar with respect to selected healthcare outcomes and/or selected population attributes in the community health measures database. The community measures scoring tool may be configured to represent similar or dissimilar communities by juxtaposing geographical representations of scores for corresponding communities on a map display, and/or by displaying a table of similar and dissimilar communities, for example. Degrees of similarity or dissimilarity between a selected community and other communities may be represented by different colors and/or different shading on a map display, or may be indicated as numerical scores in a table, for example. This allows users to select a community, and determine what are the other communities that are most similar or least similar to the selected community in terms of a range of health outcomes and/or population attributes.

In one example according to an aspect of the present disclosure, a clinical translation and trial tool is configured to represent community similarity scores to identify appropriate locations for piloting or testing medical devices, drugs or other innovations. Favorable locations for piloting or testing a new drug or health care innovation may be chosen based on their likelihood of furnishing a sufficiently large test population that is correlated to one or more selected attributes, for example. The clinical translation and trial tool also helps stakeholders chose favorable locations for implementing innovations based on favorable results of piloting or testing the innovation in a similar community.

The tools and methods described herein enable healthcare stakeholders such as communities, government agencies, insurance companies, health care networks and/or health care plans to make appropriate decisions to increase health care value. The tools and methods described herein may be used to evaluate stakeholder performance with respect to certain actionable aspects of affecting cost and health care use compared and compare the stakeholder's performance to certain benchmarks or to the performance of other stakeholders, for example. By quantifying the performance of stakeholders relative to a particular market segment, the stakeholders may improve assessments of their own market performance versus market potential, for example.

The tools and methods described herein may also be used by healthcare stakeholders to evaluate how efficiently they are using available resources to generate favorable healthcare outcomes. This allows stakeholders to identify gaps in the distribution of key resources, improve resource allocation and identify actions that may be limiting their performance.

According to an aspect of the present disclosure, the community health measures tool allows a user to select healthcare outcomes and/or population attributes, and automatically displays a representation of corresponding community healthcare measures that allow the user to easily recognize communities that stand out in terms of the selected healthcare outcomes and/or population attributes. The community health measures tool also allows a user to select particular communities so that measures of corresponding healthcare outcomes and population attributes of the communities can be automatically displayed for comparison on a geographical map, a table, and/or a heat map, for example.

Figure 3A:
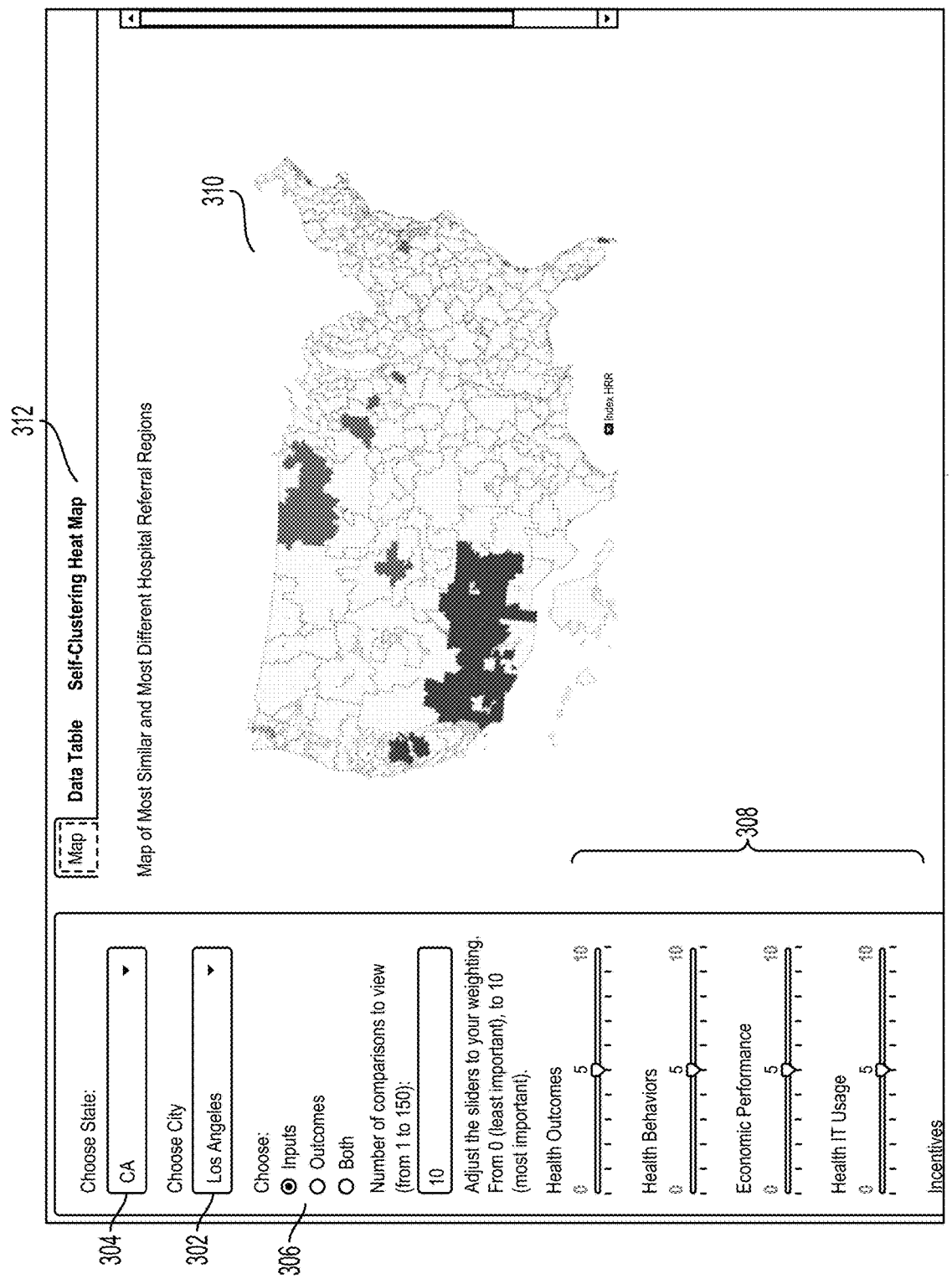
FIGS. 3A and 3B are illustrations of an interactive user interface including user controls for generating a geographical map representation of community health measures according to aspects of the present disclosure.

An example implementation of an interactive community health measure tool for identifying similar communities in terms of health care outcomes and population attributes according to an aspect of the present disclosure is described with reference to FIG. 3A. The system includes one or more user input fields, such as lists, check boxes and sliders to receive interactive input from a user and generates a representation of communities having similar or dissimilar community health measures based on the interactive input. In the example shown in FIG. 3A, a city selection input field 302 and a state selection input field 304 allow a user to easily select a city and state as a base community for comparing with other communities. A comparison basis selection input field 306 allows a user to select whether health care outcomes or inputs or both will be used as a basis of comparison for computing degrees of community similarity. The inputs may include population attributes that drive health care cost and quality in a community, for example. Population attributes that may be used as inputs for comparison include health behaviors, provider supply, social capital economic performance, provider incentives, HIT adoption and provider integration, for example. According to an aspect of the present disclosure one or more sliders 308 are provided to receive a weight selection for one or more of the population attributes to be compared. This allows a user to interactively assign greater weight to more important population attributes and to assign less weight to less important population attributes for generating the comparison and identifying communities similar to the selected base community.

According to an aspect of the present disclosure, a representation of comparative communities 310 is automatically generated and displayed based on the parameters selected in the input fields. The representation 310 automatically updates in response to changes in any of the input fields. The representation may include a geographic map display, a data table or a heat map, for example. According to an aspect of the present disclosure, a display selection input field 312 allows a user to select which type of representation to be displayed. In this example, the representation 310 shows that the communities highlighted in one color are most similar to the selected community of Los Angeles in terms of the inputs that contribute to a health care result. The communities that are highlighted in another color are the least similar to Los Angeles in terms of the same inputs.

Figure 3B:
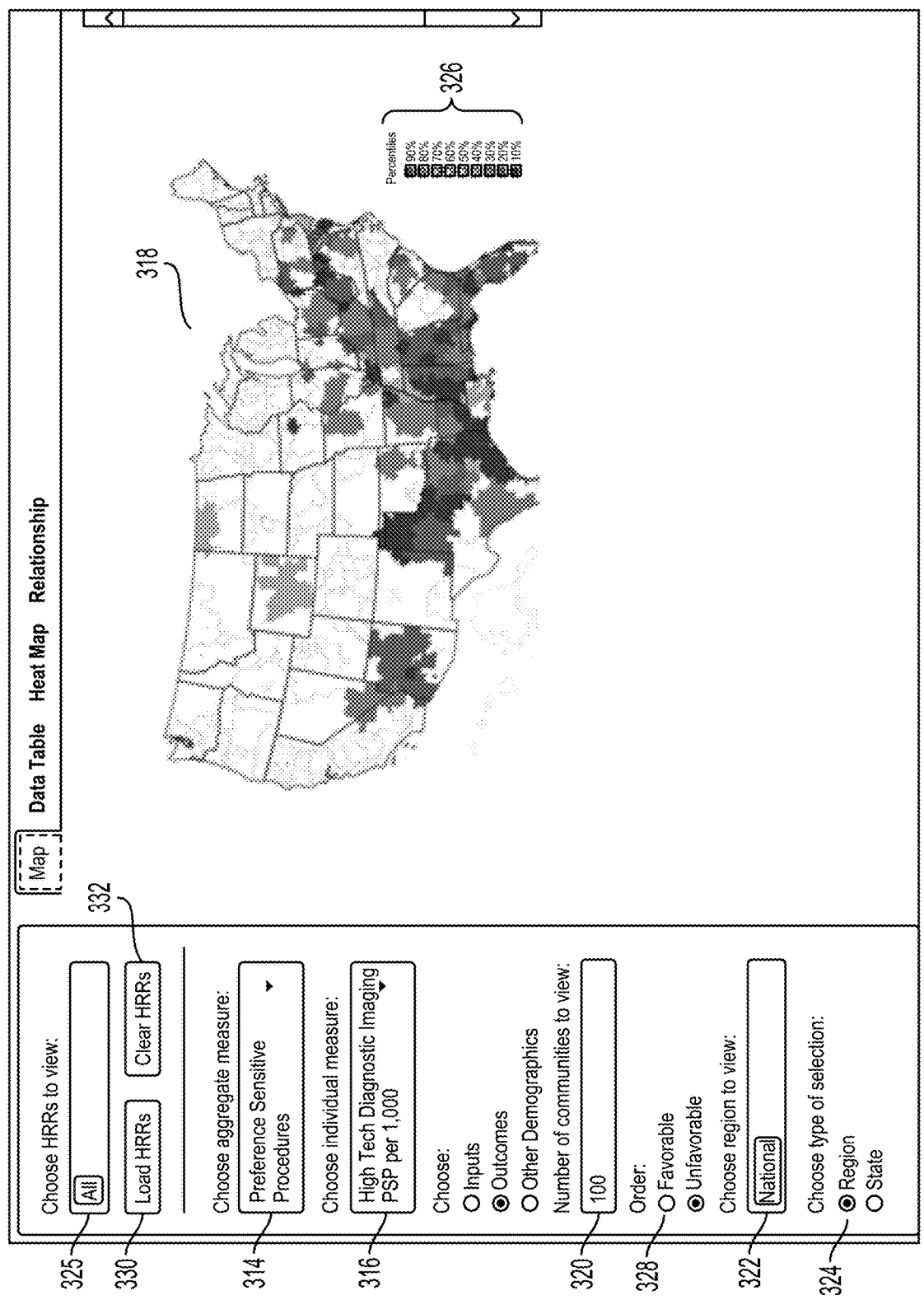

Another example implementation of an interactive community health measures tool for identifying communities based on a selected health measure is described with reference to FIG. 3B. An aggregate measures selection input field 314 and an individual measures selection input field 316 allow a user to easily select a healthcare measures as a basis for comparing communities on a representation 318. In this example the selected aggregate measure is a measure of preference sensitive procedures and the selected individual measure is a measure of high tech diagnostic imaging. A display limit field 320 allows a user to select a number of communities to be represented on the representation 318. A region selection input field 322 and a geographic area type selection field 324 allow a user to select the geographical region to be displayed. The selection of displayed regions may be further refined by a hospital referral region (HRR) selection field 325.

According to an aspect of the present disclosure, a representation of the selected healthcare measures is automatically generated and displayed in a map representation 310 of the selected regions. The representation of the selected healthcare measures may include a color coding and/or shading gradient of regions on the map representation based on a level of the selected measure. A measures key 326 displays an association of the shading or color coding of displayed regions with a corresponding level or range of levels of the selected measure. In this example, the levels are percentiles of the selected measure. The levels may displayed in order of favorable levels or unfavorable levels based on an order selection input field 328. A load data button 330 and a clear data button 332 allows users to clear the representation 318 and change the displayed representation 318 based upon different input selections.

Figure 4A:
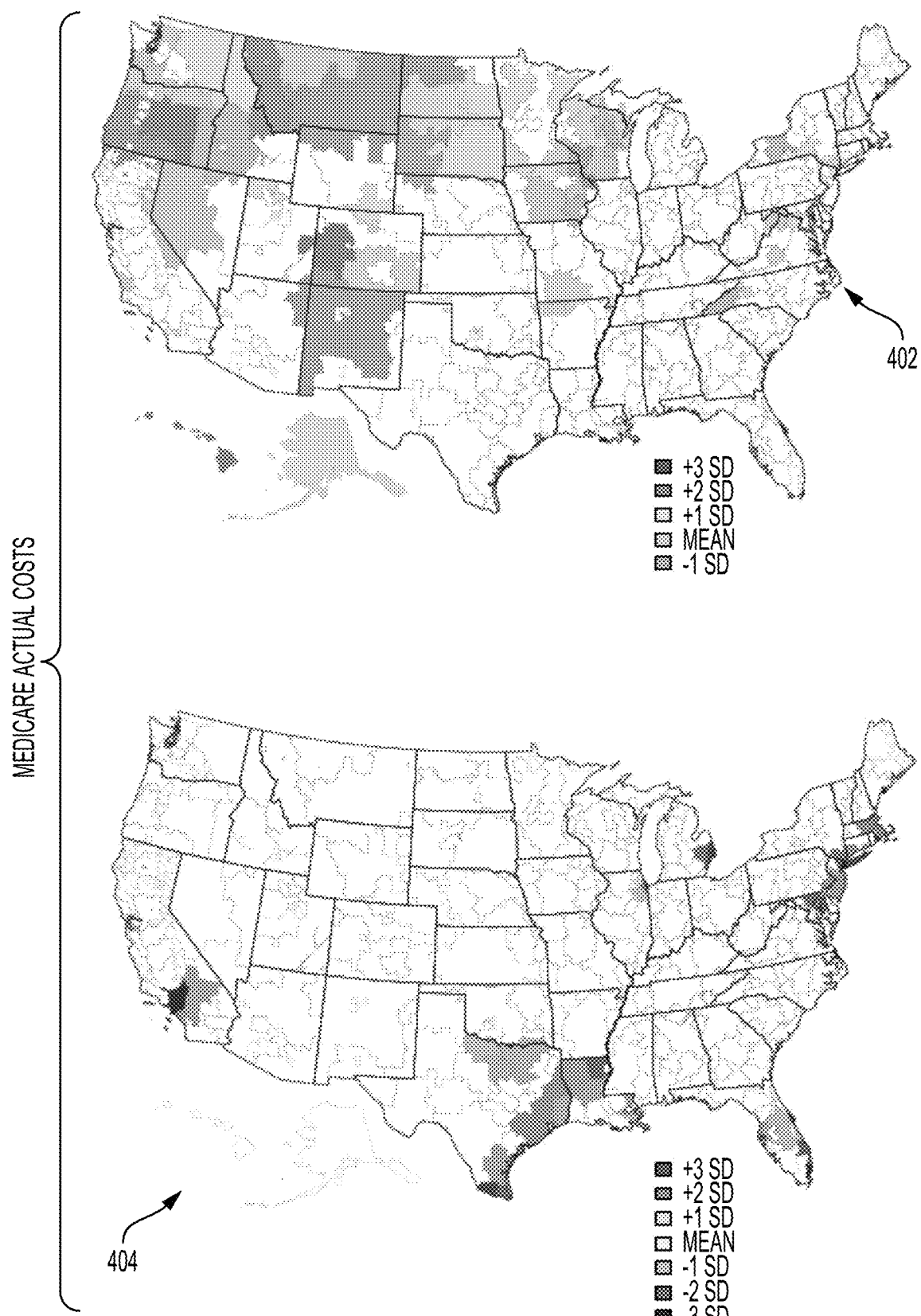
FIGS. 4A and 4B are geographical representations of community health measures generated according to aspects of the present disclosure.
Figure 4B:
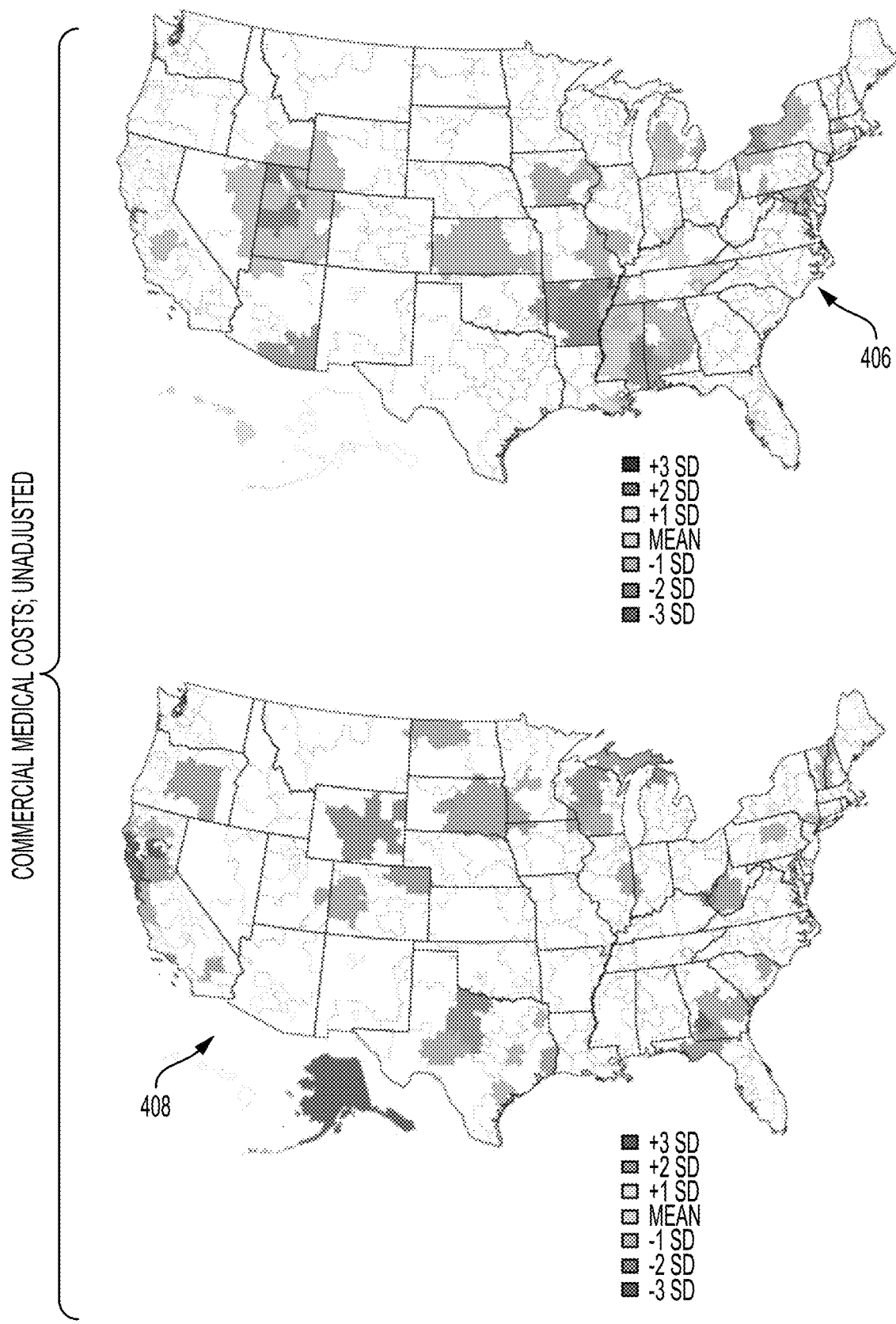

An example implementation of an interactive community health measure tool to generate geographical map representations of healthcare measures according to aspects of the present disclosure is described with reference to FIGS. 4A and 4B in which the displayed measures indicate comparative population Medicare costs and commercial healthcare costs. Referring to FIG. 4A a first geographical map representation 402 indicates communities that have relatively low population Medicare costs. The first geographical map representation 402 is juxtaposed with a second geographical map representation 404 showing communities that have relatively high population Medicare costs. Referring to FIG. 4B a third geographical map representation 406 displays communities that have relatively low population commercial medical costs. The third geographical map representation 406 is juxtaposed with fourth geographical map representation 408 showing communities that have relatively high population commercial costs. The comparative costs are displayed by color coding the communities based on their standard deviation from mean community costs. These geographical map representation allows health care policy makers and other stakeholders to identify comparative high performing communities and comparatively low performing communities for analyzing equity of resource distribution, identifying where certain opportunities or needs exist, and/or identifying where certain policies have a particular level of effect, for example.

The community health measures tool may be implemented to quickly generate custom geographical map representations of health care measures by interactively selecting parameters for comparison from a vast database of community healthcare measures. Examples of other geographic map representations of community health measures generated according to aspects of the present disclosure include geographic map representations of medication adherence, health system integration and technology adoption, avoidable hospitalizations, prevalence of smokers and prevalence of particular illness, such as emphysema, for example.

Figure 5A:
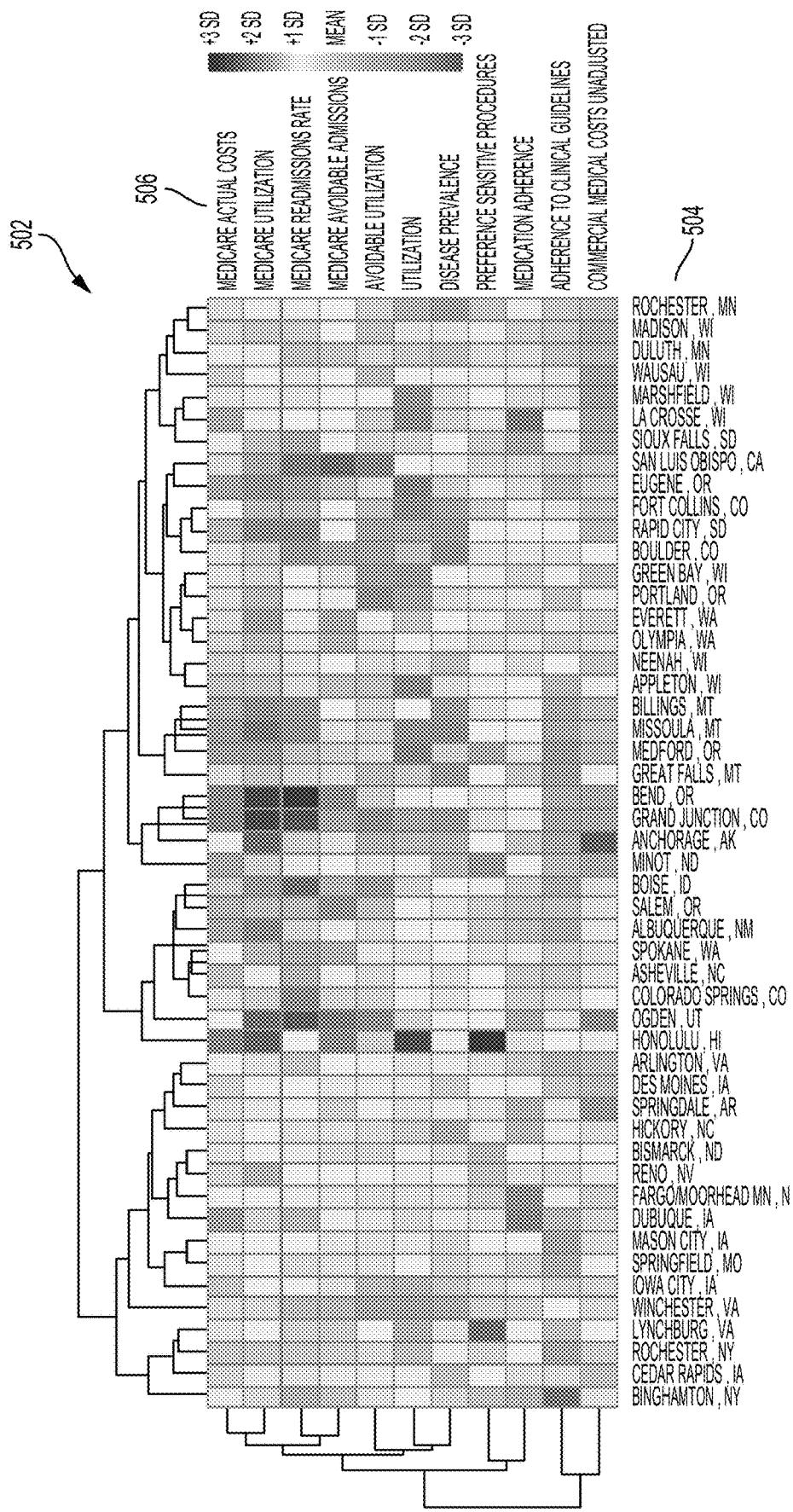
FIGS. 5A and 5B are heat map representations of community health measures generated according to aspects of the present disclosure.

An example implementation of an interactive community health measure tool to generate heat map representations of healthcare measures according to aspects of the present disclosure is described with reference to FIGS. 5A and 5B. Referring to FIG. 5A, a first heat map representation 502 includes an array of grid elements that are each color coded to represent a scores for one of a number population attributes and health outcomes for each of a number of corresponding communities. In this example, a first heat map representation 502 includes communities 504 that are identified, using the community health measures tool, as the fifty communities represented in a community health measures database as having the lowest Medicare total costs. The displayed population attributes 506 and health outcomes include measures of Medicare costs and measure of commercial medical costs, for example.

Figure 5B:
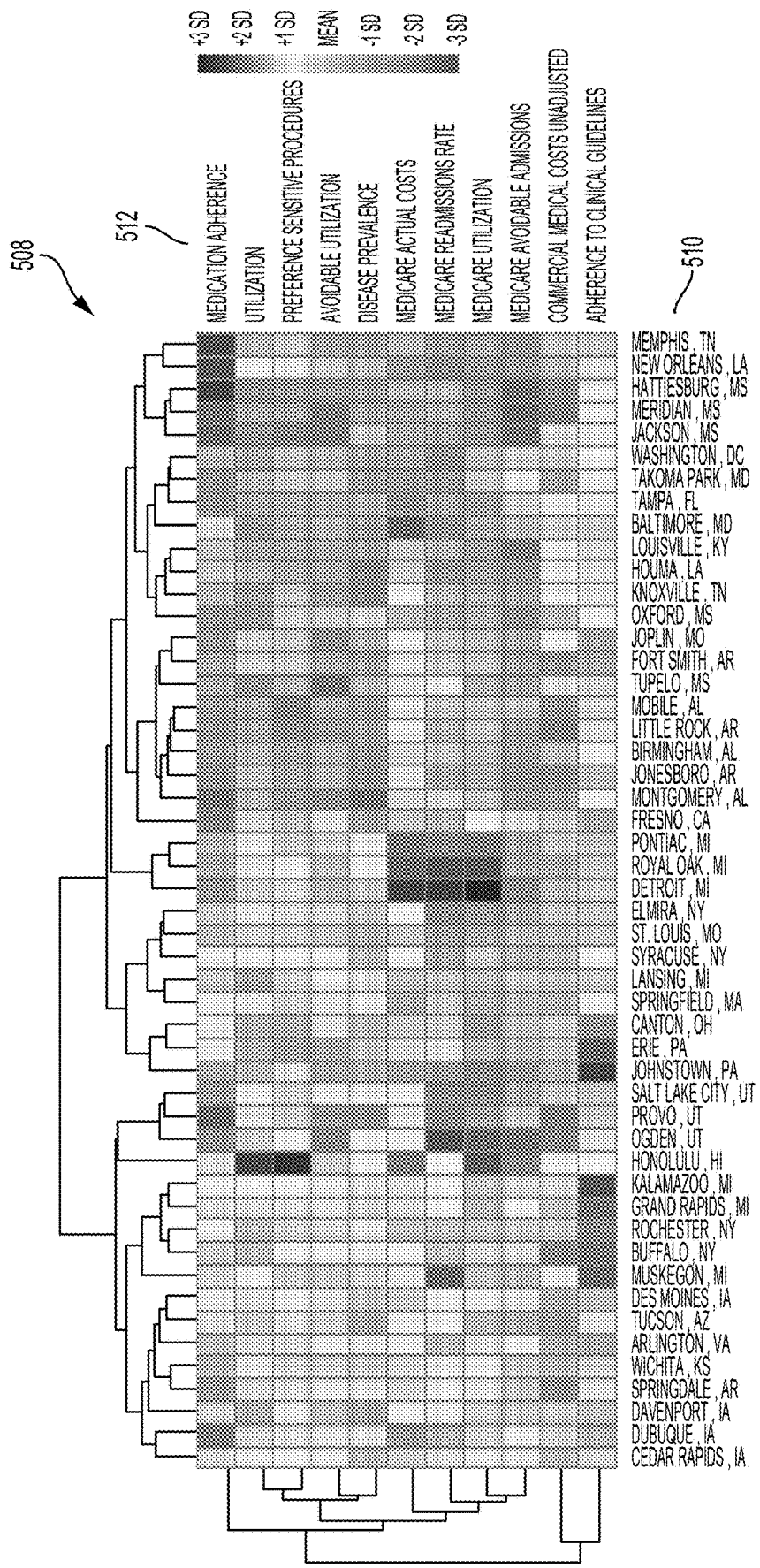

Referring to FIG. 5B, a second heat map representation 508 includes communities 510 that are identified, using the community health measures tool, as the fifty communities represented in the community health measures database as having the lowest commercial medical costs. The displayed population attributes 512 and health outcomes include measures of Medicare costs and measure of commercial medical costs, for example. By analyzing the first heat map 502 and the second heat map 508, it may be observed that communities having low Medicare costs often have high commercial costs and vice versa.

According to aspects of the present disclosure, the heat map functionality of the community health measures tool allows users to interactively cluster together attributes/factors and identify which attributes/factors that act similarly in a particular group of communities, and to identify which communities are most similar to each other, for example relative to other communities. The resulting heat map representations can be used to identify patterns of data that are otherwise substantially undetectable.

To assist pattern recognition, various clustering techniques may be applied to the information displayed in a heat map representation. In FIGS. 5A and 5B, brackets are displayed at the periphery of each heat map representation 502, 508 to indicate groupings of the displayed communities 504, 510 and groupings of the displayed population attributes and health outcomes 506, 502. In this example, the brackets are automatically generated using a grouping algorithm. The informative clustering patterns can be useful for improved hypothesis generation and addressing disparities between communities, for example.

Clustering can be performed based on any number of the attributes in the Community Health Measures Project database. Examples of other heat map representations of community health measures generated according to aspects of the present disclosure include representations different communities in terms of ethnicity and income, for example.

Geographic map representations generated by the community health measures tool may often be used together with heat map representations generated by the community health measures tool according to aspects of the present disclosure. In some implementation the complementary geographic map representations and heat map representations may provide a more robust comparison of communities.

Figure 6:
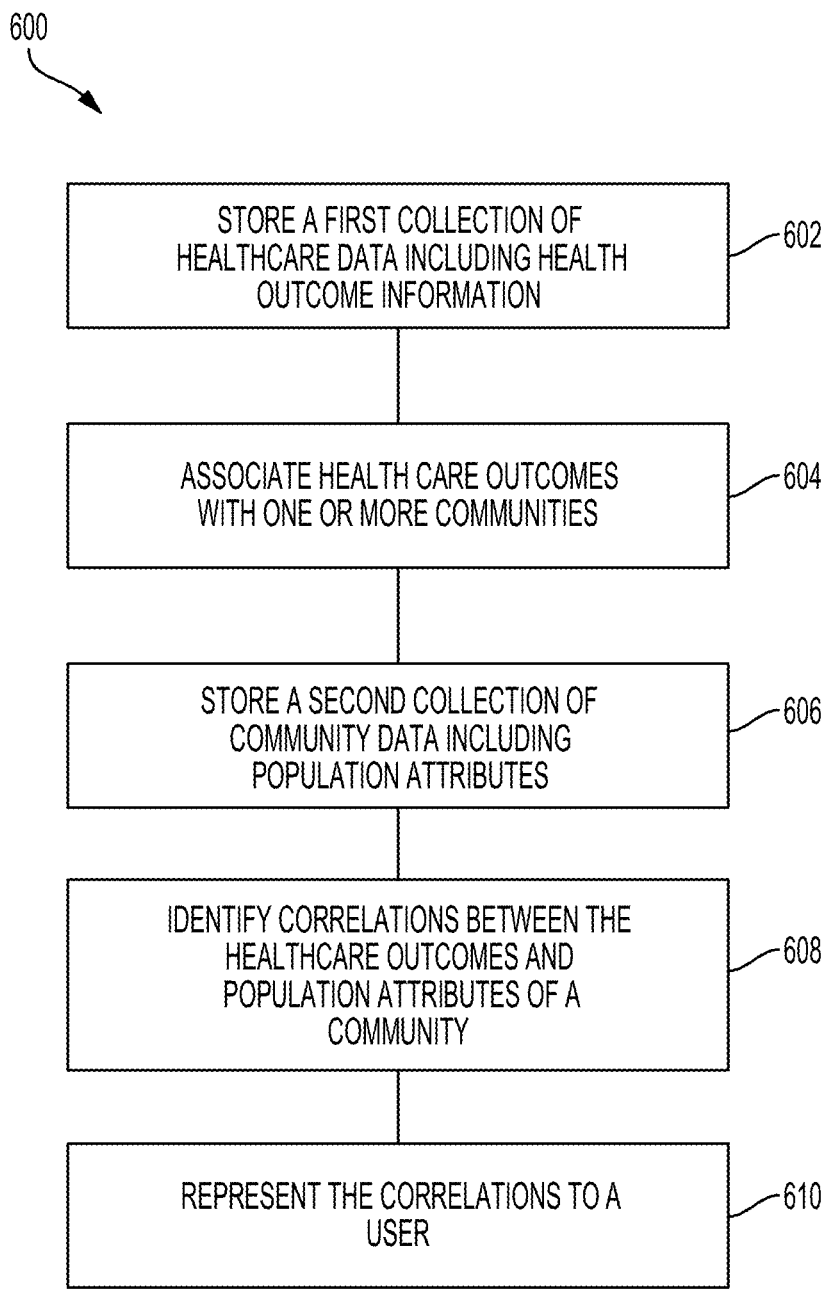
FIG. 6 is a process flow diagram illustrating a method for measuring community healthcare attributes according to aspects of the present disclosure.

A method for measuring community health care attributes according to an aspect of the present disclosure is described with reference to FIG. 6. The method 600 includes storing a first collection of health care data in one or more electronic storage systems at block 602. The first collection includes a number of health outcomes for health care consumers in a number of communities. The health care outcomes may include measures of health care cost, health care quality, and population health, for example.

At block 604, the method includes associating the health care outcomes for each consumer with one or more of the communities to generate a community health care database. At block 606, the method includes storing a second collection of community data in the one or more electronic data storage systems. The second collection includes a number of population attributes that characterize the health care consumers in each of the communities. The second collection may also include a number of population attributes that characterizes health care providers in each of the communities. The population attributes may include measure of social capital, economics, demographics, health behaviors, health care provider capacity, health care provider incentives, integration and alignment of health care providers, and health information technology, for example.

At block 608, the method includes identifying a correlation between one or more of the health care outcomes and one or more of the population attributes by accessing the first collection of health care data and the second collection of community data. At block 610, the method includes representing the correlation to a user.

The method 600 for measuring community health care attributes may also include assigning an outcome rank to each of the health care outcomes based on a predetermined hierarchy of outcomes to generate an enhanced community health care database, and representing one or more of the communities in association with one or more corresponding outcome ranks assigned to a respective healthcare outcome in the respective community.

According to another aspect of the present disclosure, the method 600 may also include assigning a population attribute rank to each of the population attributes, and representing one or more of the communities based on the ranking of one or more of the population attributes associated with the respective communities. The method 600 may also include computing a correlation between selected health care outcomes with selected population attributes and identifying similar communities based on a result of the correlating.

According to another aspect of the present disclosure, the method 600 may also include receiving an input that selects one or more of the population attributes and/or one or more of the health care outcomes, and interactively computing the correlation in response to receiving the input.

Figure 7:
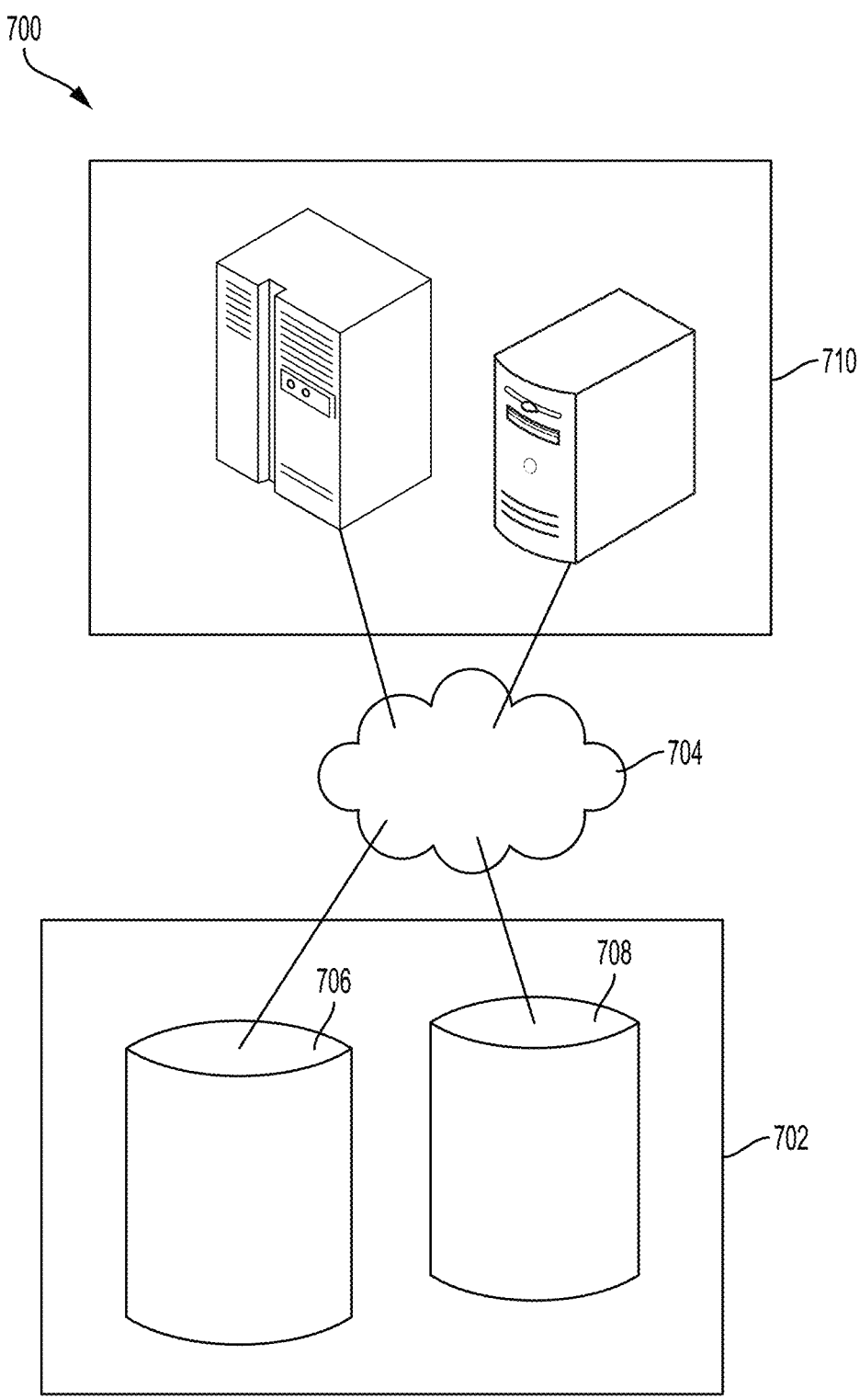
FIG. 7 is a system block diagram illustrating a system for measuring healthcare related characteristics of a population segment according to aspects of the present disclosure.

A system for measuring health care related characteristics of a population segment according to an aspect of the present disclosure is described with reference to FIG. 7. The system 700 includes one or more electronic data storage systems 702 coupled to one or more health care networks 704. A community health care database is stored in the electronic data storage system(s) 704. The community health care database including a first collection of health care data 706. The first collection of health care data 706 includes a number of health outcomes for health care consumers in a number of communities. The health care outcomes for each consumer are associated with one or more of the communities. A second collection of community data 708 is also stored in one or more of the electronic data storage systems 704. The second collection of community data 708 includes a number of population attributes that characterize the health care consumers in each of the communities. One or more processors 710 are coupled in electronic communication with the electronic data storage systems 704.

According to aspects of the present disclosure the processor(s) 710 are configured for receiving a first interactive input that selects one or more of the health care outcomes and/or one or more of the population attributes. The health care outcomes may include measures of health care cost, health care quality, and population health, for example. The population attributes may include measure of consisting of social capital, economics, demographics, health behaviors, health care provider capacity, health care provider incentives, integration and alignment of health care providers, and health information technology, for example.

The processor(s) 710 may also be configured for identifying a correlation between the selected health care outcomes and one or more of the population attributes by accessing the first collection of health care data and the second collection of community data in response to receiving the interactive inputs, and representing the correlation to a user. According to an aspect of the present disclosure, the processor(s) 710 may be configured to interactively compute the correlation in response to receiving the input.

According to an aspect of the present disclosure, the processor(s) 710 may also be configured to assign a population attribute rank to each of the population attributes, and represent one or more of the communities based on the ranking of one or more of the population attributes associated with the respective communities. The processor(s) 710 may also be configured to assign an outcome rank to each of the health care outcomes based on a predetermined hierarchy of outcomes to generate an enhanced community health care database and represent one or more of the communities in association with one or more corresponding outcome ranks assigned to a respective healthcare outcome in the respective community. According to another aspect of the present disclosure, the processor(s) 710 may be configured to identify similar communities based on a result of the correlating.

Another aspect of the present disclosure includes a method of measuring community health care characteristics. According to this aspect, the method includes receiving one or more health care outcomes for each of a number of communities, automatically scoring each of the communities based on the corresponding health care outcomes, and displaying a representation of the communities arranged based on their score. The method may also include receiving one or more population attributes that characterize the health care consumers in each of the communities, and displaying in indication of the corresponding population attributes in the representation of the communities.

According to one aspect of the present disclosure, the method includes receiving an input that selects one or more of the population attributes and one or more of the health care outcomes; and interactively displaying a geographical representation of a relationship between the selected population attributes and the selected health care outcomes in response to receiving the input. According to another aspect of the present disclosure, the method includes receiving an input that selects a number of the population attributes, and interactively displaying a heat map representation of health care measures based on the selected population attributes for each of a number of communities in response to receiving the input. The method may also include generating clustering information defining relationships between the displayed health care measures and rearranging the heat map representation based on the clustering information.

A method for measuring community health care attributes according to another aspect of the present disclosure includes storing a first collection of health care data in one or more electronic storage systems and associating the health care outcomes for each consumer with one or more of the communities to generate a community health care database. The first collection includes a number of health outcomes for health care consumers in a number of communities. The method may also include identifying a correlation between a first one of the health care outcomes associated with a community and a second one of the health care outcomes associated with the community. The method then includes representing the correlation to a user.

According to an aspect of the present disclosure, the method for measuring community health care attributes may also include storing a second collection of community data in the one or more electronic data storage systems. The second collection may include a number of population attributes that characterize the health care consumers in each of the communities and/or a number of population attributes that characterizes health care providers in each of the communities, for example. According to one aspect of the present disclosure, the method includes identifying a correlation between a first one of the population attributes and a second one of the population attributes and representing the correlation to a user. According to another aspect of the present disclosure, the method includes identifying a correlation between one or more of the health care outcomes and one or more of the population attributes by accessing the first collection of health care data and the second collection of community data and representing the correlation to a user.

The method may also include statistically processing the health care outcomes to generate a number of categories of health care outcomes and/or statistically processing the population attributes to generate a number of categories of population attributes. According to one aspect of the present disclosure, the health care outcomes are grouped into a number of categories, including measures of health care cost, measures of health care quality, and measures of population health, for example. According to another aspect of the present disclosure, the population attributes are grouped into a number of categories including measure of social capital, measures of economics, measures of demographics, measures of health behaviors, measures of health care provider capacity, measures of health care provider incentives, measures of integration of health care providers, measures of alignment of health care providers, and measures of health information technology, for example.

The method for measuring community health care attributes may also include assigning an outcome score to each of the health care outcomes based on a predetermined hierarchy of outcomes and computing a composite outcome score for each community by statistically combining the outcome scores in each community respective community. The method may also include representing one or more of the communities based a respective composite outcome score of the respective communities.

According to another aspect of the present disclosure, the method includes assigning a population attribute score to each of the population attributes, and computing a composite population attribute score for each community by statistically combining the population attribute scores in each respective community. The method may also include representing one or more of the communities based on the composite population attribute score of the respective communities. The method may also include computing a community efficiency score by statistically comparing the composite population attribute score of the community with the composite outcome score of the community. For example, the method may include computing community efficiency scores for each of a number of communities by statistically comparing the composite population attribute score of each of the communities with the composite outcome score of each respective one of the communities and displaying the community efficiency scores for each of the communities.

According to an aspect of the present disclosure, the method includes displaying a geographical representation of a relationship between selected health outcomes and/or selected population attributes. According to another aspect of the present disclosure, the method includes displaying a heat map representation of health care measures based on selected health care outcomes and/or selected population attributes. The heat map representation includes a composite outcome score indication and/or a composite population attribute score indication for each of a number of the communities. The method may also include computing clustering information that defines relationships between the displayed health care measures and rearranging the heat map representation based on the clustering information.

A method for measuring community health care attributes according to another aspect of the present disclosure includes storing a first collection of community data in the one or more electronic data storage systems. The first collection including a number attributes that characterize health care consumers in each of a number of communities. The method also includes associating the attributes that characterize the health care consumers with one or more of the communities to generate a health care community population attribute database, identifying a correlation between a first one of the attributes in a community and a second one of the attributes in the community by accessing the health care community population attribute database and representing the correlation to a user.

According to another aspect of the present disclosure, a community health measures correlations tool, herein also called "the correlation tool," allows a user to select a single measure from a set of community health measures in the community health measures database as a main variable and automatically compares the selected main variable against all of the other variables measures in the set of community health measures to identify positive correlations between any of the other variables and the selected main variable. This allows a user to systematically understand the strength of the relationship e.g., the correlation between a community variable or outcome and all other community variables or outcomes.

An example implementation of an interactive community health measure correlation tool for automatically identifying correlations between a selected main community health measures in the community health measures database and some or all other measures in the community health measures database according to an aspect of the present disclosure is described with reference to FIG. 8.

According to aspects of the present disclosure, the correlation tool includes an interactive user interface including user controls for selecting community health measures to be correlated over number of different communities. The interactive user interface includes one or more user input fields, such as lists, check boxes and sliders to receive interactive input from a user and automatically generates a representation of communities located on a graph according to the value of selected health measures in the communities. In this example implementation of the interactive community health measure relationship tool, the term hospital referral region (HRR) is used instead of the term "community." A main measure input field 802 allows a user to easily select a particular community healthcare measure to be considered as the main variable by the interactive community health measure correlation tool. In this example, the main measure input field 802 includes a drop down menu of aggregate measures 804 that allows a user to choose a general category of community health measures from which to select the main measure. In this example, the main measure input field 802 also includes a list of selectable measure types, that allows a user to select the type of measure to be selected as the main measure. The type of measure may include input measures, output measures and measures of other demographics in the community health measures. A drop down menu of particular community health measures 808 in the chosen general category and chosen type of measure of community health measures is automatically generated and displayed. The first measure input field 802 allows a user to quickly and easily select the main measure from a long list of community health measures.

According to aspects of the present disclosure, the community health measures correlation tool also includes one or more community selection input fields. The community selection input fields allow users to select a set of communities to be correlated with the selected main measure. In the example shown in FIG. 8, community selection input fields include a region selection field 818, a list of selectable community types 820, and a hospital referral region (HRR)

selection field 822. The region selection field 818 allows a user to select a region of interest, which includes the communities to be correlated with the selected main measure. The list of selectable community types 820 allows a user to select a type of region that includes the communities to be represented. The HRR selection field 822 allows a user to select a set of HRRs to be considered by the correlation tool. The number of communities to be correlated with the selected main measure based on user selection in the community selection input fields is displayed in a selected community count output field 825. A load HRR button 824 and a clear HRR button 826 allow users to respectively load or clear community health measures for the selected communities.

According to aspects of the present disclosure, each community health measure in a set of community health measures is automatically and separately correlated with the selected main measure for the selected set of communities. The automatic correlation implements conventional correlation methodologies to generate $R^2$ values representing the strength of correlation between respective community health measures and the selected main measure for each community health measure. The automatic correlation may include a positive correlation computation or negative correlation computation based on a user selection in a correlation type selector field 838. This allows a user to identify major correlations are on a positive basis.

A ranked correlation list of the community health measures 830 is automatically generated and displayed based on the generated $R^2$ values for the respective community health measures. The ranked correlation list 830 includes a name of each community health measure 832, the $R^2$ value 834 generated for the corresponding community health measure and a rank 836 of the corresponding community health measure, in which the rank of a community health measure is based on its $R^2$ value.

Automatic regeneration of the correlation list 830 may be initiated when communities are selected or changed by a user changing selections in the community selection input fields and/or when the load HRR button 824 is selected by a user, for example.

In the example shown in FIG. 8, the selected main measure in the main measure selection field 802 is "% in Poverty" and the selected correlation type in the correlation type selector field 838 is positive correlation. In this example, the correlation tool implements a positive correlation algorithm to automatically and separately compute a correlation between the % in Poverty and each other community health measure in the community health measures database for each community in the selected set of 306 communities. FIG. 8 shows a first page of the resulting correlation list 830. The first page includes the top ten community health measures that are most strongly correlated % in poverty measures of a community.

According to another aspect of the present disclosure, a community health measures relationship tool, herein also called "the relationship tool," provides a user interface that allows a user to easily select healthcare outcomes and/or population attributes from the community health measures database to be compared and correlated. The relationship tool automatically determines correlations of the selected healthcare outcomes and/or population attributes over a set communities that is easily selectable by a user. The relationship tool allows a user to quickly and easily identify relationships between and among community health measures such community factors, demographic factors and healthcare outcomes while controlling for the effects of other community factors, demographic factors and outcomes. This allows the user to isolate the unique power of a given community health measure (independent variable) to explain the variation in another community health measure (dependent variable). According to an aspect of the present disclosure, the relationship tool automatically computes relationship information between selected community health measures and presents the relationship information in the form of two graphs. One of the graphs shows the relationship between the independent and dependent variables before controlling for other variables. The other graph shows the remaining variation explained by the independent variable after controlling for the variation explained by one or more other variables.

A user of the relationship tool may select a first community health measure and a second community health measure from an interactively updated list of healthcare outcomes and population attributes in the community healthcare database for a set of communities based. A first one of the selected measures may be considered as an independent variable and a second one of the selected measures may be considered as a dependent variable, having a value that is dependent on the first variable in each community. In response to a user selecting the first community health measure and the second community health measure, the relationship tool automatically displays a representation of communities in terms of the selected measures.

According to an aspect of the present disclosure, the representation may include a correlation graph showing each community in the set of selected communities as a data point in a graph location that is determined by the values of the selected first measure and the selected second measure. An $R^2$ value representing strength of correlation between the selected values may also be displayed on the correlation graph. A regression line is automatically displayed on the graph extending through the representation of communities. The regression line is automatically generated to show the correlation between the selected first measure and second measure. The regression line and representation of communities allows the user to easily recognize correlations between the selected first measure and the selected second measure, for example. An $R^2$ value representing strength of correlation between the selected values may also be displayed on the graph.

Aspects of the present disclosure apply standard regression and partial regression methodologies to compute the correlations between selected community health measures. The computation may be performed using the well-known R programming language and/or various other traditional statistical processing methodologies. For example, the $R^2$ value and regression line may be computed using linear regression techniques or other well-known techniques for computing correlations.

An example implementation of an interactive community health measure relationship tool for automatically identifying correlations between selected community health measures according to an aspect of the present disclosure is described with reference to FIG. 9. According to aspects of the present disclosure, the relationship tool includes an interactive user interface including user controls for selecting community health measures to be correlated over number of different communities. The interactive user interface includes one or more user input fields, such as lists, check boxes and sliders to receive interactive input from a user and automatically generates a representation of communities located on a graph according to the value of selected health measures in the communities. In this example implementation of the interactive community health measure relationship tool, the term hospital referral region (HRR) is used instead of the term "community." A first measure input field 902 allows a user to easily select a particular community healthcare measure to be considered as an independent variable by the interactive community health measure relationship tool. In this example, the first measure input field 902 includes a drop down menu of aggregate measures 904 that allows a user to choose a general category of community health measures from which to select the first measure. In this example, the first measure input field 902 also includes a list of selectable measure types, that allows a user to select the type of measure to be selected as the first input measure. The type of measure may include input measures, output measures and measures of other demographics in the community health measures. A drop down menu of particular community health measures 908 in the chosen general category and chosen type of measure of community health measures is automatically generated. The first measure input field 902 allows a user to quickly and easily select the first measure from a long list of community health measures.

A second input field 910 allows the user to easily select a particular community healthcare measure to be considered as a dependent variable by the interactive community health measures relationship tool. In this example, the second measure input field 910 also includes a dropdown menu of aggregate measures 912, and a list of selectable measure types 914. A drop down menu of particular community health measures 916 in the chosen general category and chosen type of measure of community health measures is automatically generated for selecting the second measure. The second measure input field 910 allows a user to quickly and easily select the second measure, to be considered as a dependent variable by the community health measures relationship tool, from a list of community health measures.

According to aspects of the present disclosure, the community health measures relationship tool also includes one or more community selection input fields. The community selection input fields allow users to select a set of communities to be represented on a correlation graph in a location determined by the selected first measure and second measure. In the example shown in FIG. 9, community selection input fields include a region selection field 918, a list of selectable community types 920, and a hospital referral region (HRR) selection field 922. The region selection field 918 allows a user to select a region of interest, which includes the communities to be represented. The list of selectable community types 920 allows a user to select a type of region that includes the communities to be represented. The HRR selection field 922 allows a user to select a set of HRRs to be represented in the relationship tool. The number of communities to be viewed based on user selection in the community selection input fields is displayed in a selected community count output field 925. A load HRR button 924 and a clear HRR button 926 allow users to respectively load or clear community health measures for the selected communities.

The correlation tool automatically displays representations of each of the selected communities on a graph position that depends on the value of the selected first measure and the value of the selected second measure for the respective community. Automatic regeneration of a display may be initiated when communities are selected or changed by a user changing selections in the community selection input fields and/or when the load HRR button 924 is selected by a user, for example.

Figure 9:
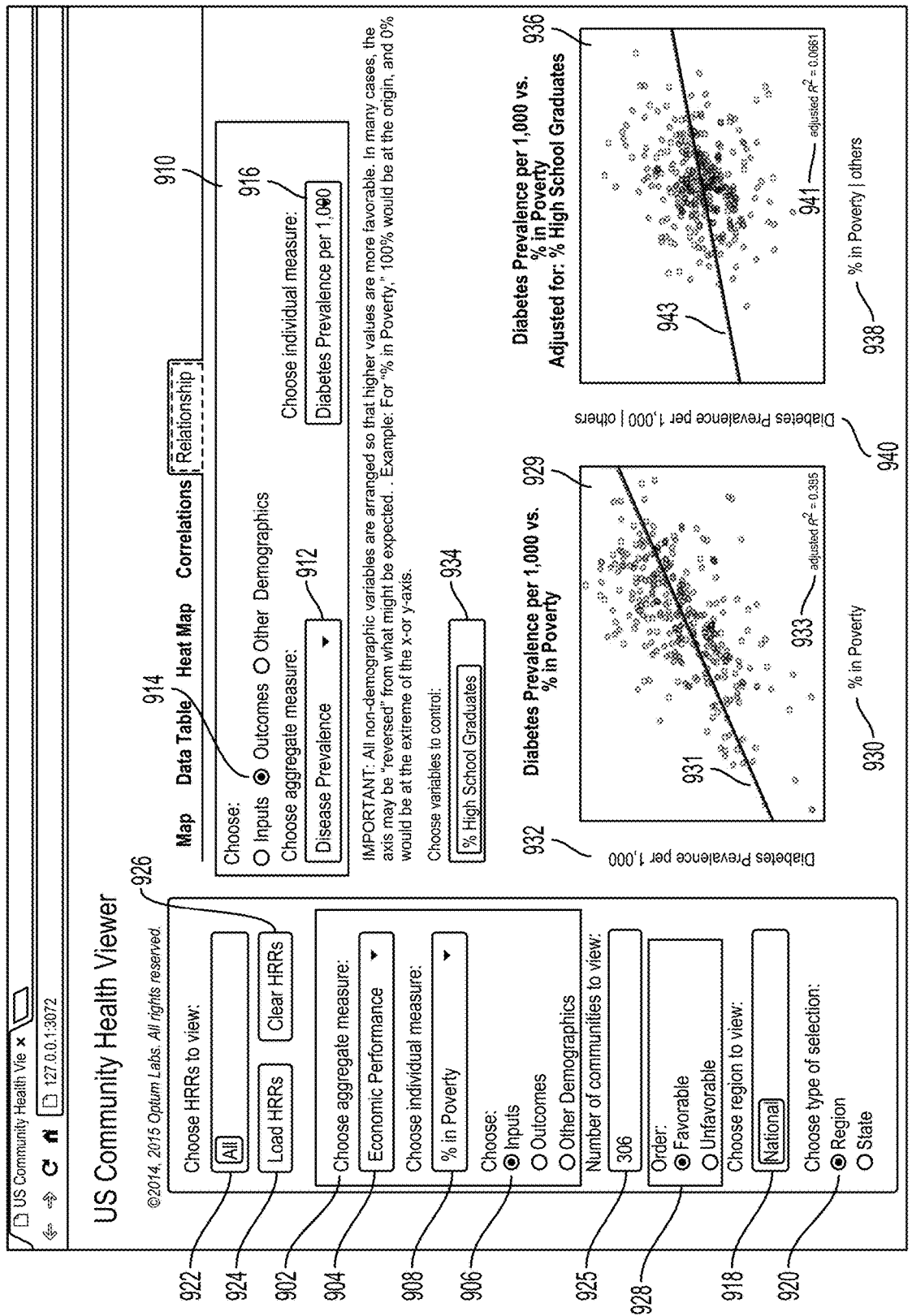
FIG. 9 is an illustration of a relationship tool user interface according to aspects of the present disclosure.

In the example shown in FIG. 9, a first measure corresponding to an independent variable is represented on a the horizontal axis of the correlation graph and a second measure corresponding to a dependent variable is represented on the vertical axis of the correlation graph. The selected set of communities may be represented in the correlation graph in order of most favorable or most unfavorable data for the selected first measure and second measure. The order of representation may be selected by a user input to an order selection field 928.

In the example shown in FIG. 9, the selected aggregate measure in the drop down menu of aggregate measures 904 for a first measure is "Economic Performance." In response to the user selection of this aggregate measure, the dropdown menu of community health measures 908 includes a list of economic performance measures. In this example the community health measure that is selected as the first measure is "% in Poverty". The selected aggregate measure in the drop down menu of aggregate measures 912 for a second measure is "Disease Prevalence". In response to the user selection of this aggregate measure, the dropdown menu of community health measures 916 includes a list of disease prevalence measures. In this example the selected community health measure selected as the second measure is "Diabetes Prevalence per 1000".

In the example shown in FIG. 9, a first correlation graph 929 is automatically generated based on the selected first measure and second measure. The name of the selected first measure is displayed as a horizontal axis label 930 and the name of the selected second measure is displayed as a vertical axis label 932 of the first correlation graph 929. A data point representing each community in the set of selected communities is displayed as a small circle on the first correlation graph in a location that corresponds to a value of the first measure and second measure for the respective community. A first regression line 931 and R2 value 933 is automatically computed and displayed on the first correlation graph 929 based on a computed correlation between the first measure and second measure.

According to another aspect of the present disclosure, the relationship tool includes a second correlation graph 936 that is automatically generated based on the selected first measure and second measure and based on a user selectable third measure.

To generate the second correlation graph 934, a user selects the third measure from a set of community health measures in a control variable input field 934. The third measure is then used as a control variable. According to this aspect, the relationship tool automatically generates the second correlation graph 934. The second correlation graph shows a second distribution of communities based on the first measure and second measure after adjusting for the third measure. The second correlation graph 934 may also include a second $R^2$ value 941 and a second regression line 943 representing the strength of correlation between the first measure and second measure after adjusting for effects of the third measure.

The name of the selected first measure is displayed along with a control variable name as a horizontal axis label 938 and the name of the selected second measure is displayed along with the control variable name as a vertical axis label 940 of the second correlation graph 936. A data point representing each community in the set of selected communities is displayed as a small circle on the first correlation graph in a location that corresponds to a value of the first measure and second measure for the respective community after adjusting for effects of the selected third measure as a control variable.

The second correlation graph and second $R^2$ value represents the remaining variation contributed by the second measure (independent variable) after controlling for the variation contributed by the third measure (control variable). This allows a user to quickly and easily perform a risk adjustment based on a selected control variable to determine whether the selected control variable explains residuals in the correlation of the first measure and second measure.

In the example shown in FIG. 9, the third measure selected as a control variable in the control variable input field 934 is "% High School Graduates". The first correlation graph 929 in this example shows a good correlation of $R^2=0.385$ between diabetes prevalence in a community and percent in poverty in the community. However, the second correlation graph 936 in this example shows that the correlation between diabetes prevalence in a community and percent in poverty in the community is substantially reduced to $R^2=0.0661$ when the correlation computation is controlled, i.e. adjusted to account for percentage of high school graduates value of the community. The reduced correlation indicates that effects of poverty on diabetes prevalence in a community are mostly due to effects of low high school graduation rate on diabetes prevalence in the community. This type of valuable insight explaining relationships between different community healthcare measures can be quickly and easily gained by using the relationship tool according to aspects of the present disclosure.

In the first correlation graph 929 and the second correlation graph 936 displayed by the relationship tool, the vertical axis position and horizontal axis position for selected values may be presented in ascending order or descending order depending on whether high or low values represent favorable values for the selected first measure and/or second measure. The displayed order is determined by the user's selection in the order selection field 928, in which the user may select to display favorable values or unfavorable values increasing to the right on the horizontal axis and upward on the vertical axis of the first correlation graph 929 and second correlation graph 936.

According to an aspect of the present disclosure, the community health measures relationship tool may be accessed by selecting a "relationship" tab of a combined user interface of community health measures tool. The community health measures correlation tool may be accessed by selecting the "correlation" tab of the combined user interface, for example.

Figure 10:
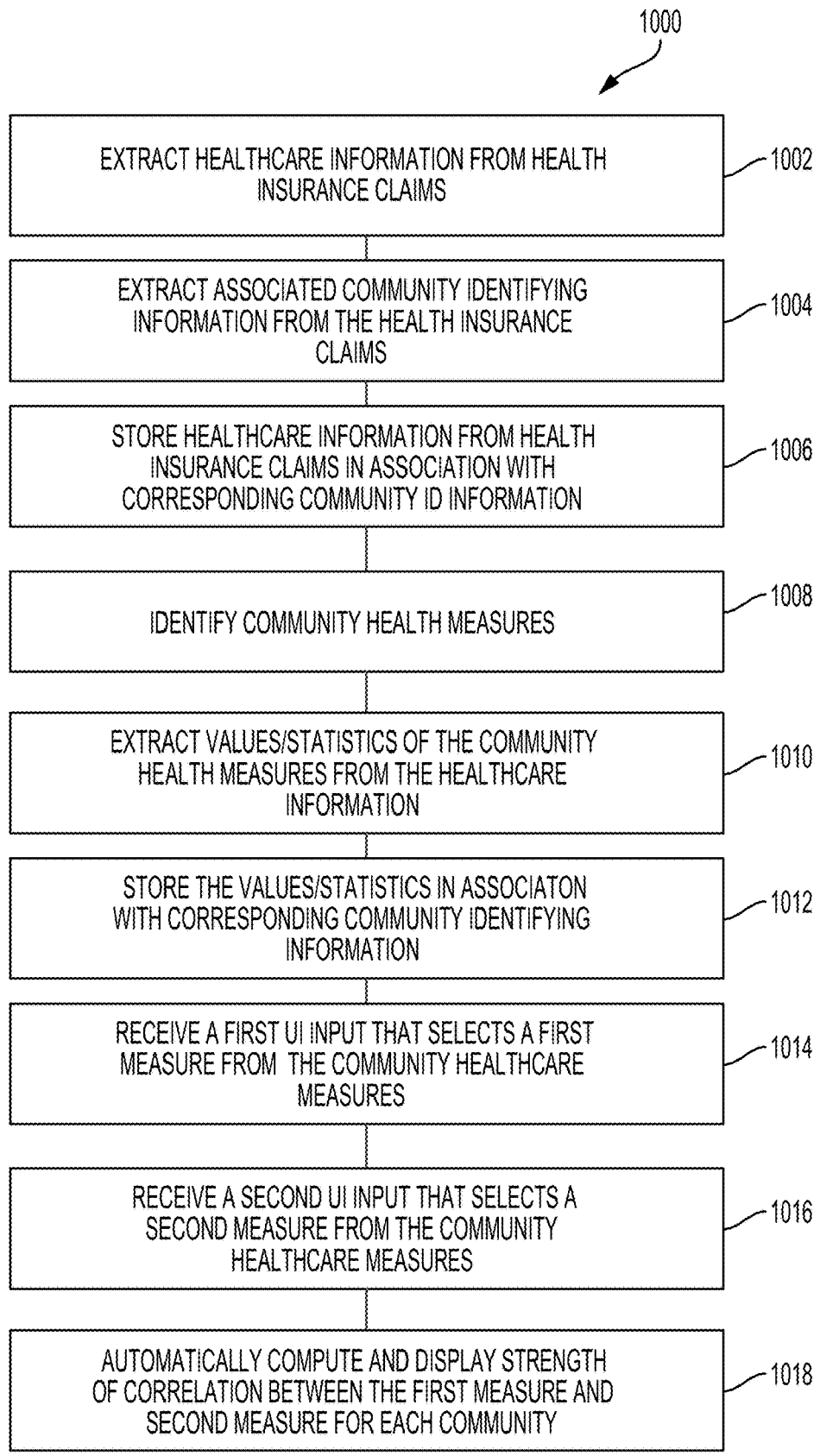
FIG. 10 is a process flow diagram illustrating a method identifying related factors affecting community healthcare attributes according to an aspect of the present disclosure.

A method for identifying related factors affecting community healthcare attributes according to an aspect of the present disclosure is described with reference to FIG. 10. The method 1000 includes extracting healthcare information from a plurality of health insurance claims at block 1002 and extracting community information associated with the healthcare information from the plurality of health claims at block 1004, wherein the community identifying information identifies one or more communities associated with the corresponding health insurance claims. At block 1006, the method includes storing the healthcare information for each of the health insurance claims in association with the community identifying information for each of the health insurance claims. At block 1008, the method includes identifying a set of community health measures including measures of the stored healthcare information. At block 1010, the method includes extracting values of one or more of the community health measures from the healthcare information. At block 1012, the method includes storing the values and/or statistics of the values for each of the communities in association with the corresponding community identifying information. At block 1014, the method includes receiving a first user interface (UI) input that selects one of the community health measures as a first measure. At block 1016, the method includes receiving a second UI input that selects another one of the community health measures as a second measure. And at block 1018, the method includes automatically computing and displaying a strength of correlation between the first measure and the second measure for the each of the communities in response to receiving the first UI input and the second UI input.

According to another aspect of the present disclosure, the method 1000 may also include receiving a third UI input that selects a subset of the communities based on the corresponding community identifying information, and automatically computing and displaying a strength of correlation between the first measure and the second measure for the selected subset of communities in response to receiving the first UI input, the second UI input and third UI inputs.

According to another aspect of the present disclosure, the method 1000 may also include, in response to receiving the first UI input, the second UI input and third UI inputs, automatically displaying a first correlation graph of data points, wherein each of the data points corresponds to a community and wherein a graph location of each of the data points is defined by a value of the first measure and a value of the second measure for the corresponding community.

According to another aspect of the present disclosure, the method 1000 may also include, in response to receiving the first UI input, the second UI input and third UI input, automatically displaying a regression line on the first correlation graph based on the computed strength of correlation.

According to another aspect of the present disclosure, the method 1000 may also include receiving a fourth UI input that selects one of the community health measures, which is not selected as the first UI input or the second UI input, as a control variable, and in response to receiving the first UI input, the second UI input, third UI input and the fourth UI input, automatically computing and displaying an adjusted strength of correlation between the first measure and the second measure for the selected subset of communities, wherein the adjusted strength of correlation is reduced compared to the strength of correlation by an amount that is attributable to a correlation between the second measure and the control variable.

According to another aspect of the present disclosure, the method 1000 may also include in response to receiving the first UI input, the second UI input and third UI input, automatically displaying a first correlation graph of data points, wherein each of the data points corresponds to a community and wherein a graph location of each of the data points is defined by a value of the first measure and a value of the second measure for the corresponding community, and in response to receiving the first UI input, the second UI input, third UI input and the fourth UI input, automatically displaying a second correlation graph of data points, wherein each of the data points corresponds to a community and wherein a graph location of each of the data points is defined by a value of the second measure and an adjusted value of the first measure based on the adjusted strength of correlation.

According to another aspect of the present disclosure, the method 1000 may also include receiving an updated first UI input that selects another one of the community health measures as a first measure or an updated second UI input that selects another one of the community health measures as the second measure or an updated third UI input that selects another subset of the communities, and automatically computing and displaying an updated strength of correlation between the first measure and the second measure for the selected communities in response to receiving the any of the updated first UI input, the second UI input or the third UI input.

According to another aspect of the present disclosure, the method 1000 may also include storing a collection of demographic information and/or healthcare resource information for each of the communities in association with the corresponding community identifying information, wherein identifying the set of community health measures further includes identifying measures of the stored demographic information and/or measures of the stored healthcare resource information for each of the communities.

Figure 11:
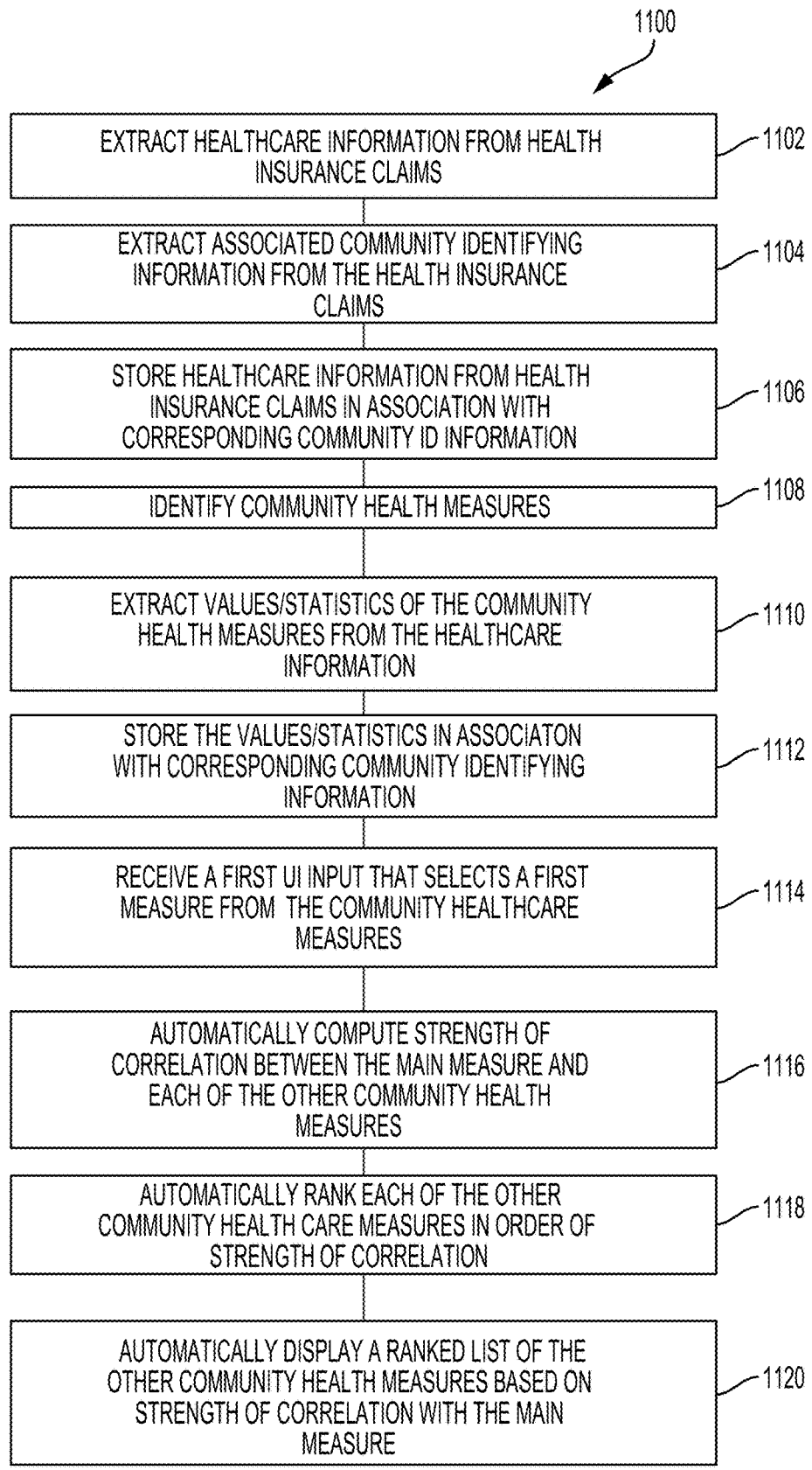
FIG. 11 is a process flow diagram illustrating a method for identifying related factors affecting community healthcare attributes according to another of the present disclosure.

A method of identifying related factors affecting community healthcare attributes according to an aspect of the present disclosure is described with reference to FIG. 11. The method 1100 includes extracting healthcare information from a plurality of health insurance claims at block 1102, and extracting community information associated with the healthcare information from the plurality of health claims at block 1104, wherein the community identifying information identifies one or more communities associated with corresponding claims in the plurality of health insurance claims. At block 1106, the method includes storing the healthcare information for each of the health insurance claims in association with the community identifying information for each of the health insurance claims. At block 1108, the method includes identifying a set of community health measures including measures of the stored healthcare information. At block 1110, the method includes extracting values of one or more of the community health measures from the healthcare information. At block 1112, the method includes storing the values and/or statistics of the values for each of the communities in association with the corresponding community identifying information. At block 1114, the method includes receiving a first user interface (UI) input that selects one of the community health measures as a main measure. At block 1116, the method includes automatically computing a strength of correlation between the main measure and each of the other community health care measures in response to receiving the first UI input. At block 1118, the method includes automatically ranking each of the other community health care measures in order of the computed strength of correlation in response to receiving the first UI input. At block 1120, the method includes automatically displaying a ranked list of the other community health care measures based on the ranking in response to receiving the first UI input.

According to another aspect of the present disclosure, the method 1100 may also include receiving a second UI input that selects a subset of the communities based on the corresponding community identifying information and automatically computing and displaying a strength of correlation between the main measure and each of the other community health care measures for the selected subset of communities in response to receiving the first UI input, the second UI input and third UI inputs.

According to another aspect of the present disclosure, the method 1100 may also include displaying the computed strength of corresponding to each of the other community health care measures and/or displaying the ranking corresponding to each of the other health care measures.

According to another aspect of the present disclosure, the method 1100 may also include receiving a third UI input that selects either a positive correlation option or a negative correlation option, computing a strength of positive correlation between the main measure and each of the other community health care measures and ranking each of the other community health care measures in order of the computed strength of positive correlation when the positive correlation option is selected or computing a strength of negative correlation between the main measure and each of the other community health care measures and ranking each of the other community health care measures in order of the computed strength of negative correlation when the negative correlation option is selected.

According to another aspect of the present disclosure, a system of identifying related factors affecting community healthcare attributes includes one or more electronic data storage systems, one or more processors in communication with the electronic data storage systems, and a user interface in communication with the processor(s). The user interface includes a display in communication with the processor(s) and an input device in communication with the processor(s). According to this aspect of the present disclosure, the processors are configured for receiving a first user interface (UI) input that selects one of a set of community health measures for a corresponding set of communities stored in the electronic data storage systems as a first measure, receiving a second UI input that selects another one of the set of community health measures for the corresponding communities stored in the electronic data storage systems as a second measure, and automatically computing and displaying on the display a strength of correlation between the first measure and the second measure for the each of the set of corresponding communities in response to receiving the first UI input and the second UI input.

According to another aspect of the present disclosure the processors may be further configured for extracting healthcare information from a plurality of health insurance claims stored in the storage systems and extracting community information associated with the healthcare information from the plurality of health claims, wherein the community identifying information identifies one or more communities associated with corresponding health insurance claims. The processors may also be configured for storing the healthcare information in the storage systems for each of the health insurance claims in association with the community identifying information for each of the health insurance claims, identifying a set of community health measures including measures of the stored healthcare information, extracting values of one or more of the community health measures from the healthcare information, and storing in the storage systems the values and/or statistics of the values for each of the communities in association with the corresponding community identifying information.

According to another aspect of the present disclosure, the processors may be configured for receiving a third UI input that selects a subset of the communities based on the corresponding community identifying information, and automatically computing and displaying on the display a strength of correlation between the first measure and the second measure for the selected subset of communities in response to receiving the first UI input, the second UI input and third UI inputs.

According to another aspect of the present disclosure, the processors may be configured for, in response to receiving the first UI input, the second UI input and third UI inputs, automatically displaying a first correlation graph of data points, wherein each of the data points corresponds to a community and wherein a graph location of each of the data points is defined by a value of the first measure and a value of the second measure for the corresponding community.

According to another aspect of the present disclosure, the processors may be configured for receiving a fourth UI input that selects one of the community health measures, which is not selected as the first UI input or the second UI input, as a control variable, and in response to receiving the first UI input, the second UI input, third UI input and the fourth UI input, automatically computing and displaying an adjusted strength of correlation between the first measure and the second measure for the selected subset of communities, wherein the adjusted strength of correlation is reduced compared to the strength of correlation by an amount that is attributable to a correlation between the second measure and the control variable. According to another aspect of the present disclosure, the processors may be configured for, in response to receiving the first UI input, the second UI input and third UI input, automatically displaying a first correlation graph of data points, wherein each of the data points corresponds to a community and wherein a graph location of each of the data points is defined by a value of the first measure and a value of the second measure for the corresponding community, and in response to receiving the first UI input, the second UI input, third UI input and the fourth UI input, automatically displaying a second correlation graph of data points, wherein each of the data points corresponds to a community and wherein a graph location of each of the data points is defined by a value of the second measure and an adjusted value of the first measure based on the adjusted strength of correlation.

According to another aspect of the present disclosure, a system of identifying related factors affecting community healthcare attributes includes one or more electronic data storage systems, one or more processors in communication with the electronic data storage systems, and a user interface in communication with the processor(s). The user interface includes a display in communication with the processor(s) and an input device in communication with the processor(s). According to this aspect, the processors are configured for extracting healthcare information from a plurality of health insurance claims, and extracting community information associated with the healthcare information from the plurality of health claims, wherein the community identifying information identifies one or more communities associated with each of the health insurance claims. The processors are further configured for storing in the data storage systems the healthcare information for each of the health insurance claims in association with the corresponding community identifying information for each of the health insurance claims andidentifying a set of community health measures including measures of the stored healthcare information. The processors are further configured for extracting values of one or more of the community health measures from the healthcare information and storing in the data storage systems, the values and/or statistics of the values for each of the communities in association with the corresponding community identifying information.

The processors are configured for receiving a first user interface (UI) input that selects one of the community health measures as a main measure. In response to receiving the first UI input, the processors are configured for automatically computing a strength of correlation between the main measure and each of the other community health care measures, automatically ranking each of the other community health care measures in order of the computed strength of correlation, and automatically displaying on the display a ranked list of the other community health care measures based on the ranking.

The terms "computer program medium" and "computer usable medium" are used to generally refer to media such a as removable storage drive and a hard disk installed in a hard disk drive. These computer program products provide software to a computer system.

Computer programs (also referred to as computer control logic) are stored in main memory and/or secondary memory. Computer programs may also be received via communications interface. Such computer programs, when executed, enable the computer system to perform the features as discussed herein. In particular, the computer programs, when executed, enable the processor to perform the features of various embodiments. Accordingly, such computer programs represent controllers of the computer system.

In various embodiments, software may be stored in a computer program product and loaded into a computer system using removable storage drive, hard disk drive or communications interface. The control logic (software), when executed by the processor, causes the processor to perform the functions of various embodiments as described herein. In various embodiments, software may be implemented in hardware components such as application specific integrated circuits (ASICs). Implementation of the hardware state machine so as to perform the functions described herein will be apparent to persons skilled in the relevant art(s).

The system contemplates uses in association with web services, utility computing, pervasive and individualized computing, security and identity solutions, autonomic computing, cloud computing, commodity computing, mobility and wireless solutions, open source, biometrics, grid computing and/or mesh computing.

Databases discussed herein may include relational, hierarchical, graphical, or object-oriented structure and/or any other database configurations. Common database products that may be used to implement the databases include DB2 by IBM (Armonk, N.Y.), various database products available from Oracle Corporation (Redwood Shores, Calif.), Microsoft Access or Microsoft SQL Server by Microsoft Corporation (Redmond, Wash.), MySQL by MySQL AB (Uppsala, Sweden), or any other suitable database product. Moreover, the databases may be organized in any suitable manner, for example, as data tables or lookup tables. Each record may be a single file, a series of files, a linked series of data fields or any other data structure. Association of certain data may be accomplished through any desired data association technique such as those known or practiced in the art. For example, the association may be accomplished either manually or automatically. Automatic association techniques may include, for example, a database search, a database merge, GREP, AGREP, SQL, using a key field in the tables to speed searches, sequential searches through all the tables and files, sorting records in the file according to a known order to simplify lookup, and/or the like. The association step may be accomplished by a database merge function, for example, using a "key field" in pre-selected databases or data sectors. Various database tuning steps are contemplated to optimize database performance. For example, frequently used files such as indexes may be placed on separate file systems to reduce In/Out ("I/O") bottlenecks.

One skilled in the art will also appreciate that, for security reasons, any databases, systems, devices, servers or other components of the system may consist of any combination thereof at a single location or at multiple locations, wherein each database or system includes any of various suitable security features, such as firewalls, access codes, encryption, decryption, compression, decompression, and/or the like.

The computers discussed herein may provide a suitable website or other Internet-based graphical user interface which is accessible by users. In various embodiments, the Microsoft Internet Information Server (IIS), Microsoft Transaction Server (MTS), and Microsoft SQL Server, are used in conjunction with the Microsoft operating system, Microsoft NT web server software, a Microsoft SQL Server database system, and a Microsoft Commerce Server. Additionally, components such as Access or Microsoft SQL Server, Oracle, Sybase, Informix MySQL, Interbase, etc., may be used to provide an Active Data Object (ADO) compliant database management system. In various embodiments, the Apache web server is used in conjunction with a Linux operating system, a MySQL database, and the PHP, and/or Python programming languages.

Any of the communications, inputs, storage, databases or displays discussed herein may be facilitated through a website having web pages. The term "web page" as it is used herein is not meant to limit the type of documents and applications that might be used to interact with the user. For example, a typical website might include, in addition to standard HTML documents, various forms, Java applets, JavaScript, active server pages (ASP), common gateway interface scripts (CGI), extensible markup language (XML), dynamic HTML, cascading style sheets (CSS), AJAX (Asynchronous Javascript And XML), helper applications, plug-ins, and the like. A server may include a web service that receives a request from a web server, the request including a URL (http://yahoo.com/stockquotes/ge) and an IP address (123.56.789.234). The web server retrieves the appropriate web pages and sends the data or applications for the web pages to the IP address. Web services are applications that are capable of interacting with other applications over a communications means, such as the Internet. Web services are typically based on standards or protocols such as XML, SOAP, AJAX, WSDL and UDDI, Web services methods are well known in the art, and are covered in many standard texts. See, e.g., ALEX NGHIEM, IT WEB SERVICES: A ROADMAP FOR THE ENTERPRISE (2003), hereby incorporated by reference.

Middleware may include any hardware and/or software suitably configured to facilitate communications and/or process transactions between disparate computing systems. Middleware components are commercially available and known in the art. Middleware may be implemented through commercially available hardware and/or software, through custom hardware and/or software components, or through a combination thereof. Middleware may reside in a variety of configurations and may exist as a standalone system or may be a software component residing on the Internet server. Middleware may be configured to process transactions between the various components of an application server and any number of internal or external systems for any of the purposes disclosed herein. WebSphere MQ™ (formerly MQSeries) by IBM, Inc. (Armonk, N.Y.) is an example of a commercially available middleware product. An Enterprise Service Bus ("ESB") application is another example of middleware.

As will be appreciated by one of ordinary skill in the art, the system may be embodied as a customization of an existing system, an add-on product, a processing apparatus executing upgraded software, a stand-alone system, a distributed system, a method, a data processing system, a device for data processing, and/or a computer program product. Accordingly, any portion of the system or a module may take the form of a processing apparatus executing code, an internet based embodiment, an entirely hardware embodiment, or an embodiment combining aspects of the internet, software and hardware. Furthermore, the system may take the form of a computer program product on a computer-readable storage medium having computer-readable program code means embodied in the storage medium. Any suitable computer-readable storage medium may be utilized, including hard disks, CD-ROM, optical storage devices, magnetic storage devices, and/or the like.

The system and method is described herein with reference to screen shots, block diagrams and flowchart illustrations of methods, apparatus (e.g., systems), and computer program products according to various embodiments. It will be understood that each functional block of the block diagrams and the flowchart illustrations, and combinations of functional blocks in the block diagrams and flowchart illustrations, respectively, can be implemented by computer program instructions.

These computer program instructions may be loaded onto a general purpose computer, special purpose computer, or other programmable data processing apparatus to produce a machine, such that the instructions that execute on the computer or other programmable data processing apparatus create means for implementing the functions specified in the flowchart block or blocks. These computer program instructions may also be stored in a computer-readable memory that can direct a computer or other programmable data processing apparatus to function in a particular manner, such that the instructions stored in the computer-readable memory produce an article of manufacture including instruction means which implement the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions specified in the flowchart block or blocks.

Accordingly, functional blocks of the block diagrams and flowchart illustrations support combinations of means for performing the specified functions, combinations of steps for performing the specified functions, and program instruction means for performing the specified functions. It will also be understood that each functional block of the block diagrams and flowchart illustrations, and combinations of functional blocks in the block diagrams and flowchart illustrations, can be implemented by either special purpose hardware-based computer systems which perform the specified functions or steps, or suitable combinations of special purpose hardware and computer instructions. Further, illustrations of the process flows and the descriptions thereof may make reference to user windows, webpages, websites, web forms, prompts, etc. Practitioners will appreciate that the illustrated steps described herein may comprise in any number of configurations including the use of windows, webpages, web forms, popup windows, prompts and the like. It should be further appreciated that the multiple steps as illustrated and described may be combined into single webpages and/or windows but have been expanded for the sake of simplicity. In other cases, steps illustrated and described as single process steps may be separated into multiple webpages and/or windows but have been combined for simplicity.

Benefits, other advantages, and solutions to problems have been described herein with regard to specific embodiments. However, the benefits, advantages, solutions to problems, and any elements that may cause any benefit, advantage, or solution to occur or become more pronounced are not to be construed as critical, required, or essential features or elements of the disclosure. The scope of the disclosure is accordingly to be limited by nothing other than the appended claims, in which reference to an element in the singular is not intended to mean "one and only one" unless explicitly so stated, but rather "one or more".

Although illustrative embodiments of the present disclosure have been described herein with reference to the accompanying drawings, it is to be understood that the present disclosure is not limited to those precise embodiments, and that various other changes and modifications may be made by one skilled in the art without departing from the scope or spirit of the disclosure.

What is claimed is:

1. A method implemented on a data processing system identifying related factors affecting geographic community health care attributes, the method comprising:
    receiving, by the data processing system, health care information from a plurality of health care claims;
    receiving, by the data processing system, community information associated with the health care information from the plurality of health care claims, the community information identifying one or more communities associated with corresponding claims in the plurality of health care claims;
    storing, by the data processing system, the health care information for each of the health care claims in association with the community identifying information for each of the health care claims;
    identifying, by the data processing system, a set of community health care measures including measures of the stored health care information;
    receiving, by the data processing system, values of one or more of the community health care measures from the health care information;
    storing, by the data processing system, the values and/or statistics of the values for each of the communities in association with the corresponding community identifying information;
    receiving, by a computer implemented application of a community measures tool having a graphical user interface, a first user interface (UI) input that selects one of the community health care measures as a first measure;
    receiving, by the computer implemented application of the community measures tool, a second UI input that selects another one of the community health care measures as a second measure;
    automatically computing, by the computer implemented application of the community measures tool, correlated data between the first measure and the second measure for the each of the communities in response to receiving the first UI input and the second UI input;
    processing, by the computer implemented application of the community measures tool, the correlated data, the processing of correlated data comprising:
        generating, by the computer implemented application of the community measures tool, a community score for the plurality of communities;
        displaying, by the graphical user interface of the computer implemented application of the community measures tool, a visual representation of the selected communities, population attributes, and health care outcomes, the visual representation comprising a first correlation graph of data points, wherein each of the data points corresponds to a community and wherein a graph location of each of the data points is defined by a value of the first measure on a horizontal axis and a value of the second measure on a vertical axis for the corresponding community;
    receiving, by the graphical user interface of the computer implemented application of the community measures tool, selection of user-defined weights for one or more of the communities, population attributes, and/or one or more of the health care outcomes to customize the visual representation and community score to the user;
    automatically updating, by the graphical user interface of the computer implemented application of the community measures tool, the visual representation of the correlated data in response to changes to the user-defined weights input to the graphical user interface of the computer implemented application;
    receiving, by the graphical user interface of the computer implemented application of the community measures tool, a user input that selects one or more of the plurality of communities from the visual representation of the selected communities, population attributes, and health care outcomes; and
    identifying, by the computer implemented application of the community measures tool, other geographic communities that are similar or dissimilar to the selected communities from the visual representation of the selected communities, population attributes, and health care outcomes on the graphical user interface based on the selected user-defined weights for one or more of the communities, population attributes, and/or one or more of the health care outcomes.

2. The method of claim 1, comprising:
    receiving a third UI input that selects a subset of the communities based on the corresponding community identifying information;
    automatically computing and displaying a strength of correlation between the first measure and the second measure for the selected subset of communities in response to receiving the first UI input, the second UI input and third UI inputs.

3. The method of claim 2, comprising:
    in response to receiving the first UI input, the second UI input and third UI input, automatically displaying a regression line on the first correlation graph based on the computed strength of correlation.

4. The method of claim 2, comprising:
    receiving a fourth UI input that selects one of the community health measures, which is not selected as the first UI input or the second UI input, as a control variable; and
    in response to receiving the first UI input, the second UI input, third UI input and the fourth UI input, automatically computing and displaying an adjusted strength of correlation between the first measure and the second measure for the selected subset of communities, wherein the adjusted strength of correlation is reduced compared to the strength of correlation by an amount that is attributable to a correlation between the second measure and the control variable.

5. The method of claim 4, comprising:
    in response to receiving the first UI input, the second UI input, third UI input and the fourth UI input, automatically displaying a second correlation graph of data points, wherein each of the data points corresponds to a community and wherein a graph location of each of the data points is defined by a value of the second measure and an adjusted value of the first measure based on the adjusted strength of correlation.

6. The method of claim 2, further comprising:
receiving an updated first UI input that selects another one of the community health care measures as a first measure or an updated second UI input that selects another one of the community health care measures as the second measure or an updated third UI input that selects another subset of the communities; and
automatically computing and displaying an updated strength of correlation between the first measure and the second measure for the selected communities in response to receiving the any of the updated first UI input, the second UI input or the third UI input.

7. The method of claim 1, comprising:
storing a collection of demographic information and/or health care resource information for each of the communities in association with the corresponding community identifying information, wherein identifying the set of community health care measures further includes identifying measures of the stored demographic information and/or measures of the stored health care resource information for each of the communities.

8. A method implemented on a data processing system identifying related factors affecting geographic communities based on community health care attributes, the method comprising:
receiving, by the data processing system, health care information from a plurality of health care claims;
receiving, by the data processing system, community information associated with the health care information from the plurality of health care claims, the community identifying information identifying one or more communities associated with each of the health care claims;
storing, by the data processing system, the health care information for each of the health care claims in association with the community identifying information for each of the health care claims;
identifying, by the data processing system, a set of community health care measures including measures of the stored health care information;
receiving, by the data processing system, values of one or more of the community health care measures from the health care information;
storing, by the data processing system, the values and/or statistics of the values for each of the communities in association with the corresponding community identifying information;
receiving, by a computer implemented application of a community measures tool having a graphical user interface, a first user interface (UI) input that selects one of the community health care measures as a main measure; and
in response to receiving the first UI input:
automatically computing, by the computer implemented application of the community measures tool, correlated data between the main measure and each of the other community health care measures;
processing, by the computer implemented application of the community measures tool, the correlated data, the processing of correlated data comprising:
generating, by the computer implemented application of the community measures tool, a community score for the plurality of communities;
displaying, by the graphical user interface of the computer implemented application of the community measures tool, a visual representation of the selected communities, population attributes, and health care outcomes, the visual representation comprising a first correlation graph of data points, wherein each of the data points corresponds to a community and wherein a graph location of each of the data points is defined by a value of the main measure on a horizontal axis and a value of a second measure on a vertical axis for the corresponding community;
receiving, by the graphical user interface of the computer implemented application of the community measures tool, selection of user-defined weights for one or more of the communities, population attributes, and/or one or more of the health care outcomes to customize the visual representation and community score to the user;
automatically updating, by the graphical user interface of the computer implemented application of the community measures tool, the visual representation of the correlated data in response to changes to the user-defined weights from the graphical user interface of the computer implemented application;
receiving, by the graphical user interface of the computer implemented application of the computer implemented application of the community measures tool, a user input that selects one or more of the plurality of communities from the visual representation of the selected communities, population attributes, and health care outcomes; and
identifying, by the computer implemented application of the community measures tool, other geographic communities that are similar or dissimilar to the selected communities from the visual representation of the selected communities, population attributes, and health care outcomes on the graphical user interface based on the selected user-defined weights for one or more of the communities, population attributes, and/or one or more of the health care outcomes;
automatically ranking, by the computer implemented application of the community measures tool, each of the other community health care measures in order of the computed strength of correlation; and
automatically displaying, by the computer implemented application of the community measures tool, a ranked list of the other community health care measures based on the ranking.

9. The method of claim 8, comprising:
receiving a second UI input that selects a subset of the communities based on the corresponding community identifying information; and
automatically computing and displaying a strength of correlation between the main measure and each of the other community health care measures for the selected subset of communities in response to receiving the first UI input, the second UI input and third UI inputs.

10. The method of claim 8, comprising:
displaying the computed strength of corresponding to each of the other community health care measures.

11. The method of claim 8, comprising displaying the ranking corresponding to each of the other health care measures.

12. The method of claim 8, comprising:
receiving a third UI input that selects either a positive correlation option or a negative correlation option;
computing a strength of positive correlation between the main measure and each of the other community health care measures and ranking each of the other community health care measures in order of the computed strength of positive correlation when the positive correlation option is selected; and
computing a strength of negative correlation between the main measure and each of the other community health care measures and ranking each of the other community health care measures in order of the computed strength of negative correlation when the negative correlation option is selected.

13. A system of identifying related factors affecting geographic communities based on community health care attributes, the system comprising:
one or more electronic data storage systems;
a processor in communication with the electronic data storage systems; and
a user interface in communication with the processor, the user interface comprising a graphical user interface (GUI) display in communication with the processor and an input device in communication with the processor;
wherein the processor is configured for:
running, by the processor, a computer implemented application of a community measures tool;
receiving, by the computer implemented application of the community measures tool via the input device, a first user interface (UI) input that selects one of a set of community health care measures for a corresponding set of communities stored in the electronic data storage systems as a first measure;
receiving, by the computer implemented application of the community measures tool via the input device, a second UI input that selects another one of the set of community health care measures for the corresponding communities stored in the electronic data storage systems as a second measure; and
automatically computing, by the computer implemented application of the community measures tool, correlated data between the first measure and the second measure for the each of the communities in response to receiving the first UI input and the second UI input;
processing, by the computer implemented application of the community measures tool, the correlated data using the community measures tool, the processing of correlated data comprising:
generating, by the computer implemented application of the community measures tool, a community score for the plurality of communities;
displaying, by the GUI display of the user interface, a visual representation of the selected communities, population attributes, and health care outcomes, the visual representation comprising a first correlation graph of data points, wherein each of the data points corresponds to a community and wherein a graph location of each of the data points is defined by a value of the first measure on a horizontal axis and a value of the second measure on a vertical axis for the corresponding community;
receiving, via the input device of the user interface, selection of user-defined weights for one or more of the communities, population attributes, and/or one or more of the health care outcomes to customize the visual representation and community score to the user;
automatically updating, by the GUI display of the user interface, the visual representation of the correlated data in response to changes to the user-defined weights from the input device;
receiving, via the input device of the user interface, a user input that selects one or more of the plurality of communities from the visual representation of the selected communities, population attributes, and health care outcomes; and
identifying, by the computer implemented application of the community measures tool, other geographic communities that are similar or dissimilar to the selected communities from the visual representation of the selected communities, population attributes, and health care outcomes on the GUI display of the user interface based on the selected user-defined weights for one or more of the communities, population attributes, and/or one or more of the health care outcomes.

14. The system of claim 13, wherein the processor is further configured for:
receiving healthcare information from a plurality of health care claims stored in the storage systems;
receiving community information associated with the health care information from the plurality of health claims, the community identifying information identifying one or more communities associated with each of the health care claims;
storing the health care information in the storage systems for each of the health care claims in association with the community identifying information for each of the health care insurance claims;
identifying a set of community health care measures including measures of the stored health care information;
receiving values of one or more of the community health care measures from the health care information; and
storing in the storage systems the values and/or statistics of the values for each of the communities in association with the corresponding community identifying information.

15. The system of claim 14, wherein the processor is configured for:
receiving a third UI input that selects a subset of the communities based on the corresponding community identifying information; and
automatically computing and displaying on the display a strength of correlation between the first measure and the second measure for the selected subset of communities in response to receiving the first UI input, the second UI input and third UI inputs.

16. The system of claim 15, wherein the processor is configured for:
receiving a fourth UI input that selects one of the community health care measures, which is not selected as the first UI input or the second UI input, as a control variable; and
in response to receiving the first UI input, the second UI input, third UI input and the fourth UI input, automatically computing and displaying an adjusted strength of correlation between the first measure and the second measure for the selected subset of communities, wherein the adjusted strength of correlation is reduced compared to the strength of correlation by an amount that is attributable to a correlation between the second measure and the control variable.

17. The system of claim 16, wherein the processor is configured for:
in response to receiving the first UI input, the second UI input, third UI input and the fourth UI input, automatically displaying a second correlation graph of data points, wherein each of the data points corresponds to a community and wherein a graph location of each of the data points is defined by a value of the second measure and an adjusted value of the first measure based on the adjusted strength of correlation.

18. A system of identifying related factors affecting a geographic community based on community health care attributes, the system comprising:
one or more electronic data storage systems;
a processor in communication with the electronic data storage systems; and
a user interface in communication with the processor, the user interface comprising a graphical user interface (GUI) display in communication with the processor and an input device in communication with the processor;
wherein the processor is configured for:
running, by the processor, a computer implemented application of the community measures tool;
receiving, by the processor, health care information from a plurality of health care claims;
receiving, by the processor, community information associated with the health care information from the plurality of health care claims, the community identifying information identifying one or more communities associated with each of the health care claims;
storing, by the processor, in the data storage systems the health care information for each of the health care claims in association with the community identifying information for each of the health care claims;
identifying, by the processor, a set of community health care measures including measures of the stored health care information;
receiving, by the processor, values of one or more of the community health care measures from the health care information;
storing, by the processor, in the data storage systems, the values and/or statistics of the values for each of the communities in association with the corresponding community identifying information;
receiving, by the computer implemented application of the community measures tool, a first user interface (UI) input that selects one of the community health care measures as a main measure;
in response to receiving the first UI input:
automatically computing, by the computer implemented application of the community measures tool, correlated data between the main measure and each of the other community health care measures;
processing, by the computer implemented application of the community measures tool, the correlated data, the processing of correlated data comprising:
generating, by the computer implemented application of the community measures tool, a community score for the plurality of communities;
displaying, by the GUI display of the user interface, a visual representation of the selected communities, population attributes, and health care outcomes, the visual representation comprising a first correlation graph of data points, wherein each of the data points corresponds to a community and wherein a graph location of each of the data points is defined by a value of the main measure on a horizontal axis and a value of a second measure on a vertical axis for the corresponding community;
receiving, via the input device of the user interface, selection of user-defined weights for one or more of the communities, population attributes, and/or one or more of the health care outcomes to customize the visual representation and community score to the user;
automatically updating, by the GUI display of the user interface, the visual representation of the correlated data in response to changes to the user-defined weights from the input device of the user interface;
receiving, via the input device of the user interface, a user input that selects one or more of the plurality of communities from the visual representation of the selected communities, population attributes, and health care outcomes; and
identifying, by the computer implemented application of the community measures tool, other geographic communities that are similar or dissimilar to the selected communities from the visual representation of the selected communities, population attributes, and health care outcomes on the GUI display of the user interface based on the selected user-defined weights for one or more of the communities, population attributes, and/or one or more of the health care outcomes;
automatically ranking, by the computer implemented application of the community measures tool, each of the other community health care measures in order of the computed strength of correlation;
automatically displaying, by the GUI display of the user interface, a ranked list of the other community health care measures based on the ranking.

* * * * *